(12) United States Patent
Kim et al.

(10) Patent No.: US 8,586,211 B2
(45) Date of Patent: Nov. 19, 2013

(54) ASYMMETRICAL ARYL AMINE DERIVATIVE FOR ORGANIC ELECTROLUMINESCENCE DEVICES, METHOD FOR PREPARING SAME, ORGANIC THIN FILM FOR ORGANIC ELECTROLUMINESCENCE DEVICES AND ORGANIC ELECTROLUMINESCENCE DEVICE USING SAME

(75) Inventors: Sang Dong Kim, Gyeonggi-do (KR); Se Hun Kim, Gyeonggi-do (KR); Ji Hye Lee, Gyeonggi-do (KR); Yong Ho Oh, Gyeonggi-do (KR)

(73) Assignee: Dongwoo Fine-Chem Co. Ltd., Jeollabuk-do (KR)

( * ) Notice: Subject to any disclaimer, the term of this patent is extended or adjusted under 35 U.S.C. 154(b) by 122 days.

(21) Appl. No.: 13/139,715

(22) PCT Filed: Dec. 16, 2009

(86) PCT No.: PCT/KR2009/007518
§ 371 (c)(1),
(2), (4) Date: Jun. 14, 2011

(87) PCT Pub. No.: WO2010/071352
PCT Pub. Date: Jun. 24, 2010

(65) Prior Publication Data
US 2012/0032152 A1 Feb. 9, 2012

(30) Foreign Application Priority Data

Dec. 18, 2008 (KR) .................. 10-2008-0129685
Aug. 5, 2009 (KR) .................. 10-2009-0071884
Dec. 14, 2009 (KR) .................. 10-2009-0124172

(51) Int. Cl.
*H01L 51/54* (2006.01)

(52) U.S. Cl.
USPC .......... 428/690; 428/917; 313/504; 313/505; 313/506; 257/40; 257/E51.05; 257/E51.026; 257/E51.032; 564/26; 564/426; 564/434; 585/27

(58) Field of Classification Search
USPC .............. 428/690, 917; 313/504, 505, 506; 257/40, E51.05, E51.026, E51.032; 564/26, 426, 434; 585/27
See application file for complete search history.

(56) References Cited

U.S. PATENT DOCUMENTS 6,660,408 B1   12/2003  Toguchi et al.
7,405,326 B2 *  7/2008  Kawamura et al. ........... 564/427
(Continued)

FOREIGN PATENT DOCUMENTS

JP    11-339963       12/1999
JP    2003-089682  *   3/2003  ............ C07C 211/57
(Continued)

*Primary Examiner* — Gregory Clark
(74) *Attorney, Agent, or Firm* — Workman Nydegger

(57) ABSTRACT

Provided are asymmetric arylamine derivatives for an organic electroluminescent element, represented by the formula (1), which is prepared by sequentially inducing a secondary amine and a tertiary amine to an aryl compound Ar core so that they do not include a symmetrical axis and a symmetrical surface in a molecule, a manufacturing method of the same, an organic thin layer material including the asymmetric arylamine derivatives, and an organic electroluminescent element employing the same:

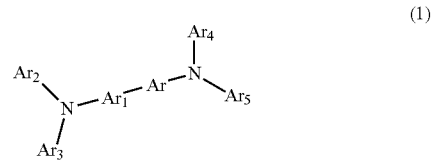

(1)

wherein Ar represents a $C_{10}$-$C_{20}$ divalent aryl group, $Ar_1$ is a divalent $C_6$-$C_{30}$ aryl group, and $Ar_2$ to $Ar_5$ each independently represents a divalent $C_6$-$C_{30}$ aryl group, at least one of $Ar_2$ to $Ar_5$ having a different structure when the secondary amine and the tertiary amine in Ar are substituted at symmetrical positions, and $Ar_2$ to $Ar_5$ having the same structure or different structures when the secondary amine and the tertiary amine in Ar are substituted at asymmetrical positions. The asymmetric arylamine derivative can be used in forming an organic thin layer for an organic electroluminescent element. When the organic electroluminescent element is formed using a dopant as an emitting material, the asymmetric arylamine derivative exhibits superb emission efficiency and an excellent lifetime characteristic in a blue wavelength region.

11 Claims, 1 Drawing Sheet

(56) References Cited

U.S. PATENT DOCUMENTS

| | | |
|---|---|---|
| 8,026,514 B2 | 9/2011 | Jang et al. |
| 8,288,014 B2 | 10/2012 | Hwang et al. |
| 8,394,511 B2 | 3/2013 | Hwang et al. |
| 2004/0265632 A1 | 12/2004 | Okinaka et al. |
| 2006/0251925 A1 | 11/2006 | Hosokawa et al. |
| 2007/0029927 A1 | 2/2007 | Kawamura et al. |
| 2007/0075635 A1 | 4/2007 | Yabunouchi et al. |

FOREIGN PATENT DOCUMENTS

| | | |
|---|---|---|
| JP | 2009-185030 | 8/2009 |
| JP | 2010-059160 | 3/2010 |
| KR | 10-2007-0104086 | 10/2007 |
| WO | WO 2008/133459 | 11/2008 |

* cited by examiner

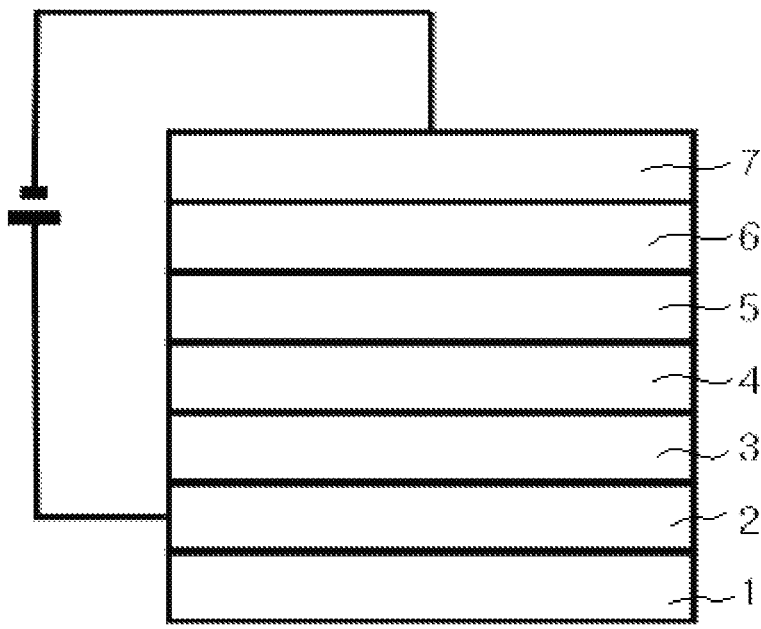

US 8,586,211 B2

ASYMMETRICAL ARYL AMINE DERIVATIVE FOR ORGANIC ELECTROLUMINESCENCE DEVICES, METHOD FOR PREPARING SAME, ORGANIC THIN FILM FOR ORGANIC ELECTROLUMINESCENCE DEVICES AND ORGANIC ELECTROLUMINESCENCE DEVICE USING SAME

CROSS-REFERENCE TO RELATED APPLICATION

This application claims priority to and the benefit of Korean Patent Application No. 10-2008-0129685 filed on Dec. 18, 2008, Korean Patent Application No. 10-2009-0071884 filed on Aug. 5, 2009, and Korean Patent Application No. 10-2009-0124172, filed on Dec. 14, 2009, the entire content of which is incorporated herein by reference.

BACKGROUND OF THE INVENTION

1. Field of the Invention

Aspects of the present invention relate to asymmetric arylamine derivatives for an organic electroluminescent (which will be occasionally referred to as "EL", hereinafter) element, a manufacturing method of the same, an organic thin layer material for an organic EL element including the asymmetric arylamine derivatives, and an organic EL element employing the same.

2. Related Art

In line with the recent trend toward large-sized display devices, demand for flat display devices occupying a reduced space is gradually increasing. Accordingly, lightness and an increased viewing angle have become more important. In this regard, an organic electroluminescent (EL) element, which is a novel flat display device, having advantages including lightness, wide viewing angle, and a high-speed response, utilizing a spontaneous light emitting phenomenon, has been attracting attention.

An organic electroluminescence device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. VanSlyke, Applied Physics Letters, Volume 51, Pages 913, 1987), many studies have been conducted on organic EL devices using organic materials as the constituting materials.

Lifetime of the organic EL element is most affected by a blue emitting material, and many attempts at improvement of lifetime have conventionally been made by improving the blue emitting material.

Among the conventional attempts, highly efficient organic EL elements have mainly been developed, which use a distyryl compound as an organic light-emitting material and additionally use styrylamine, as disclosed in WO/1994/06175. Korean Patent Publication No. KR2002-0070333 discloses a blue light emitting compound having a diphenyl anthracene structure in its skeleton and an organic EL element using the same. However, the emission efficiency and luminance of the disclosed organic EL element using the blue light emitting compound are always insufficient. In addition, U.S. Pat. No. 6,852,429, Korean Patent Publication No. 2005-0107809 and 2006-0006760 disclose an organic light emitting device using a substituted pyrene based compound, which has, however, reduced blue color purity.

Techniques for realizing a high-quality deep-blue color are disclosed, in which a phenylanthracene derivative (Japanese Patent Publication No. 1996-012600), of using a material having naphthyl groups at 9 and 10 positions of anthracene (Japanese Patent Publication No. 1999-3782), a device material having fluoranthene groups at 9 and 10 positions of anthracene (Japanese Patent Publication No. 2001-257074), or the like, are used as host materials for light emission. Although many studies of anthracene derivatives used as light emitting materials have been conducted, there remain problems that lifetime is insufficient and it is not easy to form a thin film with uniformity. Thus, excellent film forming efficiency cannot be achieved, heat resistance may be poor, and intermolecular aggregation may occur during deposition due to a planar structure. Particularly, the existing methods are not advantageous in that high efficiency, high-quality blue emission and long lifetime cannot be easily achieved.

SUMMARY OF THE INVENTION

The present invention provides an asymmetric arylamine derivative for an organic electroluminescent element, which exhibits a high efficiency of light emission and a prolonged lifetime.

The present invention also provides a manufacturing method of an asymmetric arylamine derivative for an organic electroluminescent element, which can easily prepare the aryamine derivative.

The present invention also provides an organic thin layer material for an organic electroluminescent element including the asymmetric arylamine derivatives, The present invention also provides an organic electroluminescent element employing the same.

In one embodiment of the present invention, there is provided an asymmetric arylamine derivative for an organic electroluminescent element, represented by the formula (1) with the proviso that the arylamine derivative does not include a symmetrical axis and a symmetrical surface in a molecule by inducing a secondary amine and a tertiary amine to an aryl compound (Ar) core:

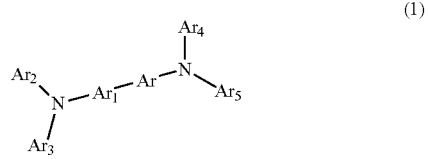

(1)

wherein Ar represents a $C_{10}$-$C_{20}$ divalent aryl group, $Ar_1$ is a divalent $C_6$-$C_{30}$ aryl group, and $Ar_2$ to $Ar_5$ each independently represents a divalent $C_6$-$C_{30}$ aryl group, at least one of $Ar_2$ to $Ar_5$ having a different structure when the secondary amine and the tertiary amine in Ar are substituted at symmetrical positions, and $Ar_2$ to $Ar_5$ having the same structure or different structures when the secondary amine and the tertiary amine in Ar are substituted at asymmetrical positions.

In the asymmetric arylamine derivative represented by the formula (1), Ar may be a divalent aryl group selected from the group consisting of naphthalene, pyrene, perylene and pentacene.

In the asymmetric arylamine derivative represented by the formula (1), Ar may be naphthalene represented by the formula (2) or pyrene represented by the formula (3):

(2)

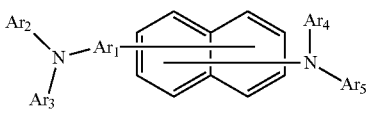

wherein Ar$_1$ is a divalent C$_6$-C$_{30}$ aryl group, and Ar$_2$ to Ar$_5$ each independently represents a divalent C$_6$-C$_{30}$ aryl group, at least one of Ar$_2$ to Ar$_5$ having a different structure when the secondary amine and the tertiary amine in naphthalene are substituted at symmetrical positions, and Ar$_2$ to Ar$_5$ having the same structure or different structures when the secondary amine and the tertiary amine in naphthalene are substituted at asymmetrical positions; and (3)

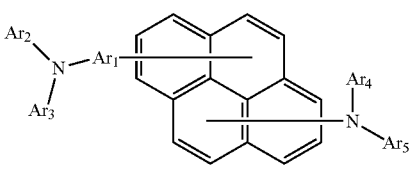

wherein Ar$_1$ is a divalent C$_6$-C$_{30}$ aryl group, and Ar$_2$ to Ar$_5$ each independently represents a divalent C$_6$-C$_{30}$ aryl group, at least one of Ar$_2$ to Ar$_5$ having a different structure when the secondary amine and the tertiary amine in pyrene are substituted at symmetrical positions, and Ar$_2$ to Ar$_5$ having the same structure or different structures when the secondary amine and the tertiary amine in pyrene are substituted at asymmetrical positions.

In the formula (1), Ar$_1$ may be an aryl group selected from the group consisting of an aryl group represented by the formula (4), an aryl group represented by the formula (5), an aryl group represented by the formula (6), an aryl group represented by the formula (7), an aryl group represented by the formula (8), an aryl group represented by the formula (9), an aryl group represented by the formula (10), an aryl group represented by the formula (11), and an aryl group in which at least two of the aryl groups represented by the formulas (4) to (11) are combined:

(4)

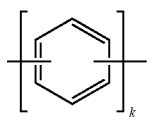

wherein k represents an integer of 1 to 3;

(5)

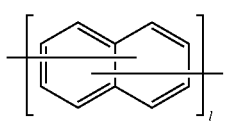

wherein l represents an integer of 1 or 2;

(6)

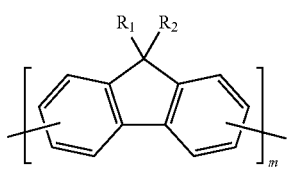

wherein m represents an integer of 1 or 2, R$_1$ and R$_2$ are each independently selected from the group consisting of a C$_1$-C$_{20}$ alkyl group, a C$_6$-C$_{20}$ cycloalkyl group capable of forming a unsaturated ring, a C$_1$-C$_{20}$ alkoxy group, and a C$_6$-C$_{12}$ aryl group;

(7)

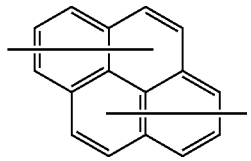

(8)

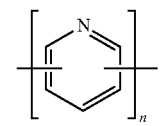

wherein n represents an integer of 1 to 3;

(9)

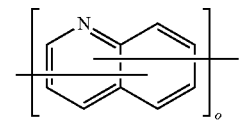

wherein o represents an integer of 1 or 2;

(10)

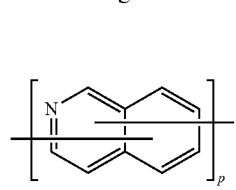

wherein p represents an integer of 1 or 2; and (11)

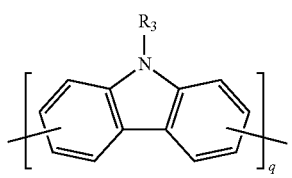

wherein q represents an integer of 1 or 2, and R$_3$ is a C$_1$-C$_{20}$ alkyl group or a C$_6$-C$_{12}$ aryl group.

Ar$_2$ to Ar$_5$ each independently may represent a divalent C$_6$-C$_{30}$ aryl group selected from the group consisting of an aryl group represented by the formula (12), an aryl group represented by the formula (13), an aryl group represented by the formula (14), an aryl group represented by the formula (15), an aryl group represented by the formula (16), an aryl group represented by the formula (17), an aryl group represented by the formula (18), an aryl group represented by the formula (19), and an aryl group in which at least two of the aryl groups represented by the formulas (12) to (19) are combined, at least one of Ar$_2$ to Ar$_5$ having a different structure when the secondary amine and the tertiary amine in Ar of the formula (1) are substituted at symmetrical positions, and Ar$_2$ to Ar$_5$ having the same structure or different structures when the secondary amine and the tertiary amine in Ar are substituted at asymmetrical positions:

(12) 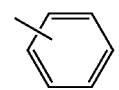

(13) 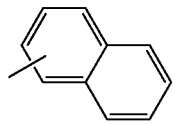

(14) 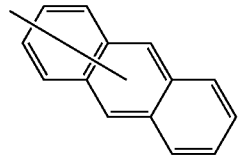

(15) 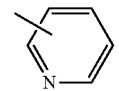

(16) 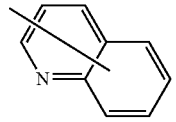

(17) 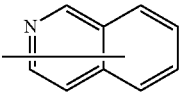

(18) 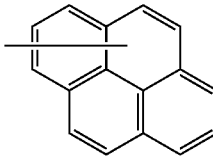

(19) 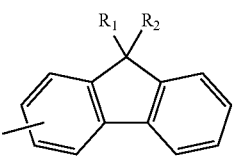

wherein $R_1$ and $R_2$ are each independently selected from the group consisting of a $C_1$-$C_{20}$ alkyl group, a $C_6$-$C_{20}$ cycloalkyl group capable of forming a unsaturated ring, a $C_1$-$C_{20}$ alkoxy group, and a $C_6$-$C_{12}$ aryl group.

Preferably, in the formula (1), Ar, $Ar_1$, $Ar_2$, $Ar_3$, $Ar_4$, and $Ar_5$ have each independently at least one hydrogen substituted by a substituent selected from the group consisting of deuterium atom, a halogen atom, a nitro group, a $C_1$-$C_{20}$ alkyl group, a $C_6$-$C_{20}$ cycloalkyl group, a $C_1$-$C_{20}$ alkoxy group, a cyano group, a trifluoromethyl group, an alkylsilyl group having a $C_1$-$C_6$ alkyl group, and an arylsilyl group having $C_4$-$C_8$ hetero atoms.

In another embodiment of the present invention, there is provided a manufacturing method of an arylamine derivative for an organic electroluminescent element, represented by the formula (1) with the proviso that the arylamine derivative does not include a symmetrical axis and a symmetrical surface in a molecule, the aryamine derivative prepared by sequentially substituting the functional groups with a secondary amine and a tertiary amine by subjecting a starting material, an aryl compound (Ar) core di-substituted with the same functional group or different functional groups to a well known process such as an aryl amination reaction or a Suzuki-coupling reaction, as represented by the following reaction scheme 1:

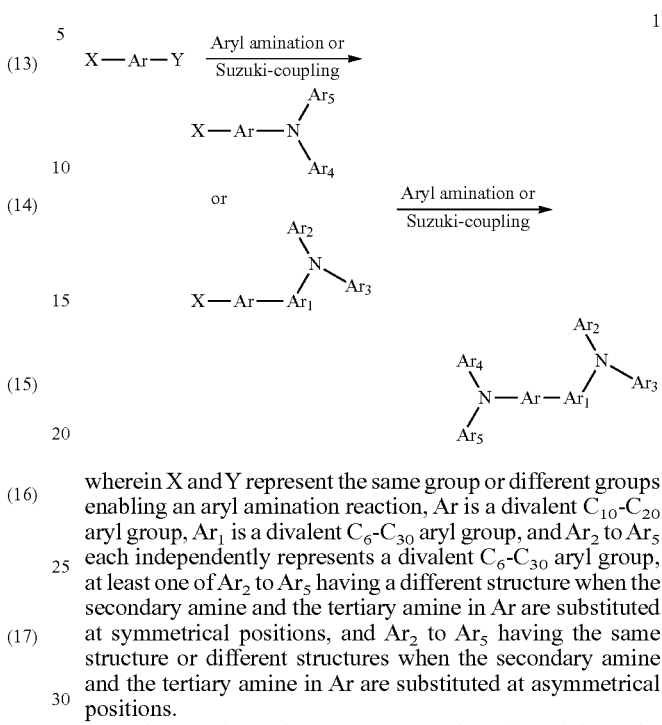

wherein X and Y represent the same group or different groups enabling an aryl amination reaction, Ar is a divalent $C_{10}$-$C_{20}$ aryl group, $Ar_1$ is a divalent $C_6$-$C_{30}$ aryl group, and $Ar_2$ to $Ar_5$ each independently represents a divalent $C_6$-$C_{30}$ aryl group, at least one of $Ar_2$ to $Ar_5$ having a different structure when the secondary amine and the tertiary amine in Ar are substituted at symmetrical positions, and $Ar_2$ to $Ar_5$ having the same structure or different structures when the secondary amine and the tertiary amine in Ar are substituted at asymmetrical positions.

In the reaction scheme 1, Ar may be selected from the group consisting of naphthalene, pyrene, perylene and pentacene. Ar may be naphthalene represented by the reaction scheme 2:

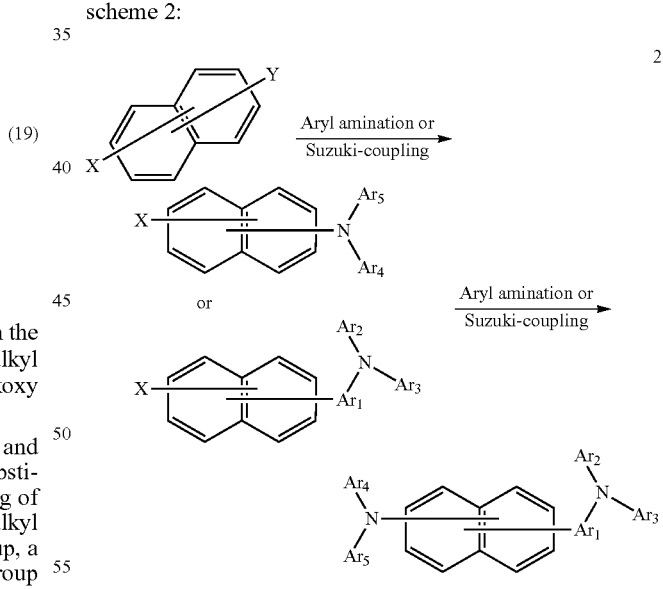

wherein X, Y and $Ar_1$ to $Ar_5$ are the same as defined above in the reaction scheme 1,
or pyrene represented by the reaction scheme 3:

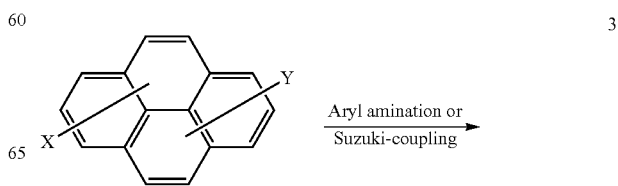

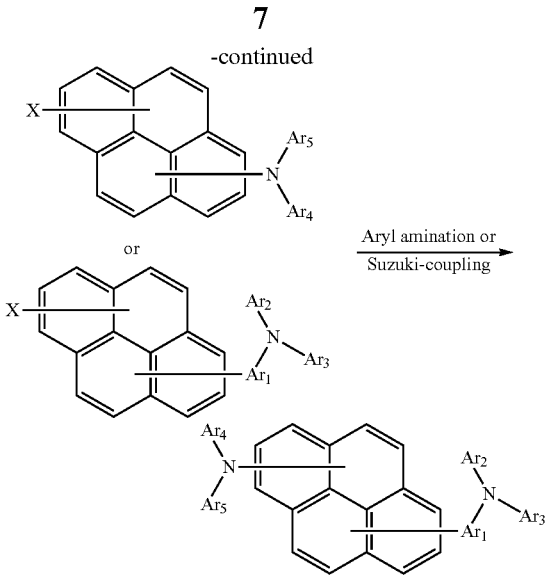

wherein X, Y and Ar₁ to Ar₅ are the same as defined above in the reaction scheme 1.

In still another embodiment of the present invention, there is provided an organic thin layer material for an organic electroluminescent element, organic thin layer material comprising the asymmetric aryamine derivative represented by the formula (1).

In still another embodiment of the present invention, there is provided an organic electroluminescent device comprising an anode, a cathode and multiple organic thin layers between the anode and the cathode, wherein at least one of the multiple organic thin layers includes the asymmetric arylamine derivative represented by the formula (1).

The multiple organic thin layers may include at least one selected from a hole injection layer, a hole transport layer, a light-emitting layer, an electron injection layer and an electron transport layer. In particular, the organic thin layers are preferably light-emitting layers. In addition, the organic thin layers may include a host compound and a dopant compound.

As described above, according to the present invention, since a secondary amine and a tertiary amine are induced to an aryl compound core of the asymmetric arylamine derivative, with the proviso that the arylamine derivative does not include a symmetrical axis and a symmetrical surface in a molecule, is provided, thereby achieving superb emission efficiency and an excellent lifetime characteristic in a blue wavelength region when it is used for an organic electroluminescent element.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below for illustration only, which thus is not limitative of the present invention, and wherein:

FIG. 1 is a schematic diagram illustrating a structure of an organic electroluminescent element according to an embodiment of the present invention.

DETAILED DESCRIPTION OF THE INVENTION

The present invention will now be described in greater detail. However, the following description serves to provide further appreciation of the invention but is not meant in any way to restrict the scope of the invention.

The present invention provides an asymmetric arylamine derivative for an organic electroluminescent element, represented by the formula (1) with the proviso that the arylamine derivative does not include a symmetrical axis and a symmetrical surface in a molecule by inducing a secondary amine and a tertiary amine to an aryl compound (Ar) core:

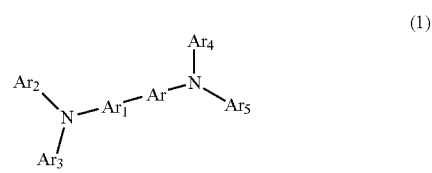

(1)

wherein Ar represents a $C_{10}$-$C_{20}$ divalent aryl group, $Ar_1$ is a divalent $C_6$-$C_{30}$ aryl group, and $Ar_2$ to $Ar_5$ each independently represents a divalent $C_6$-$C_{30}$ aryl group, at least one of $Ar_2$ to $Ar_5$ having a different structure when the secondary amine and the tertiary amine in Ar are substituted at symmetrical positions, and $Ar_2$ to $Ar_5$ having the same structure or different structures when the secondary amine and the tertiary amine in Ar are substituted at asymmetrical positions.

The Ar in the asymmetric arylamine derivative represented by the formula (1) is preferably selected from the group consisting of naphthalene, pyrene, perylene and pentacene. Particularly, the Ar in the asymmetric arylamine derivative represented by the formula (1) is more preferably is naphthalene represented by the formula (2) or pyrene represented by the formula (3):

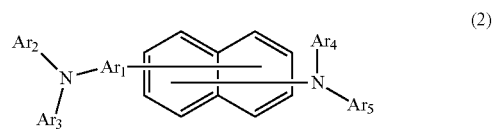

(2)

wherein $Ar_1$ is a divalent $C_6$-$C_{30}$ aryl group, and $Ar_2$ to $Ar_5$ each independently represents a divalent $C_6$-$C_{30}$ aryl group, at least one of $Ar_2$ to $Ar_5$ having a different structure when the secondary amine and the tertiary amine in naphthalene are substituted at symmetrical positions, and $Ar_2$ to $Ar_5$ having the same structure or different structures when the secondary amine and the tertiary amine in naphthalene are substituted at asymmetrical positions; and

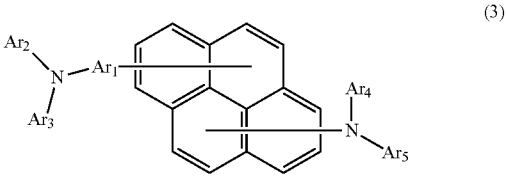

(3)

wherein $Ar_2$ to $Ar_5$ are the same as defined above in the formula (2), except that naphthalene is replaced by pyrene.

In the formula (1), $Ar_1$ is an aryl group selected from the group consisting of an aryl group represented by the formula (4), an aryl group represented by the formula (5), an aryl group represented by the formula (6), an aryl group represented by the formula (7), an aryl group represented by the formula (8), an aryl group represented by the formula (9), an aryl group represented by the formula (10), an aryl group represented by the formula (11), and an aryl group in which at least two of the aryl groups represented by the formulas (4) to (11) are combined:

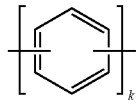
(4)

wherein k represents an integer of 1 to 3;

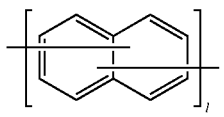
(5)

wherein l represents an integer of 1 or 2;

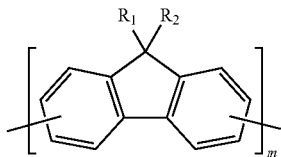
(6)

wherein m represents an integer of 1 or 2, $R_1$ and $R_2$ are each independently selected from the group consisting of a $C_1$-$C_{20}$ alkyl group, a $C_6$-$C_{20}$ cycloalkyl group capable of forming a unsaturated ring, a $C_1$-$C_{20}$ alkoxy group, and a $C_6$-$C_{12}$ aryl group;

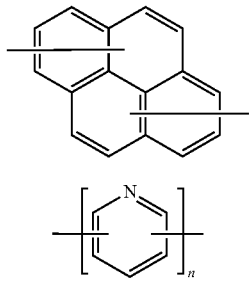
(7)

(8)

wherein n represents an integer of 1 to 3;

(9)

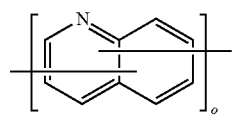

wherein o represents an integer of 1 or 2;

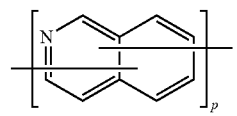
(10)

wherein p represents an integer of 1 or 2; and

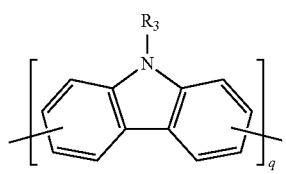
(11)

wherein q represents an integer of 1 or 2, and $R_3$ is a $C_1$-$C_{20}$ alkyl group or a $C_6$-$C_{12}$ aryl group.

In the formula (1), $Ar_2$ to $Ar_5$ each independently represents a divalent $C_6$-$C_{30}$ aryl group selected from the group consisting of an aryl group represented by the formula (12), an aryl group represented by the formula (13), an aryl group represented by the formula (14), an aryl group represented by the formula (15), an aryl group represented by the formula (16), an aryl group represented by the formula (17), an aryl group represented by the formula (18), an aryl group represented by the formula (19), and an aryl group in which at least two of the aryl groups represented by the formulas (12) to (19) are combined, at least one of $Ar_2$ to $Ar_5$ having a different structure when the secondary amine and the tertiary amine in Ar of the formula (1) are substituted at symmetrical positions, and $Ar_2$ to $Ar_5$ having the same structure or different structures when the secondary amine and the tertiary amine in Ar are substituted at asymmetrical positions:

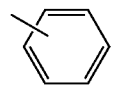
(12)

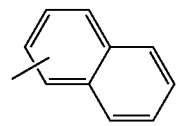
(13)

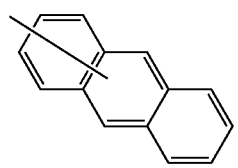
(14)

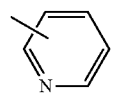
(15)

(16) 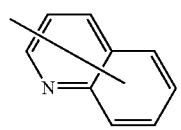

(17) 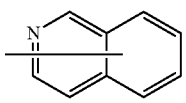

(18) 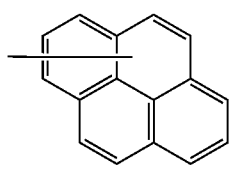

(19) 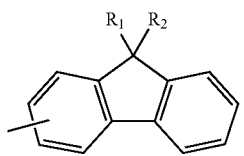

wherein $R_1$ and $R_2$ are each independently selected from the group consisting of a $C_1$-$C_{20}$ alkyl group, a $C_6$-$C_{20}$ cycloalkyl group capable of forming a unsaturated ring, a $C_1$-$C_{20}$ alkoxy group, and a $C_6$-$C_{12}$ aryl group.

Preferably, in the formula (1), Ar, $Ar_1$, $Ar_2$, $Ar_3$, $Ar_4$, and $Ar_5$ have each independently at least one hydrogen substituted by a substituent selected from the group consisting of deuterium atom, a halogen atom, a nitro group, a $C_1$-$C_{20}$ alkyl group, a $C_6$-$C_{20}$ cycloalkyl group, a $C_1$-$C_{20}$ alkoxy group, a cyano group, a trifluoromethyl group, an alkylsilyl group having a $C_1$-$C_6$ alkyl group, and an arylsilyl group having $C_4$-$C_8$ hetero atoms.

Examples of the compound represented by the formula (2) when Ar in the derivative represented by the formula (1) is naphthalene include, but not limited to, the following structures represented by the formulas (20) to (25):

<Naphthalene Derivatives>

<20> 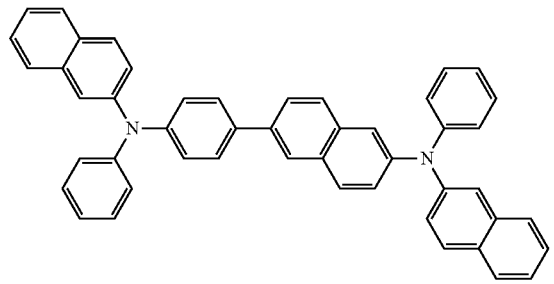

<21> 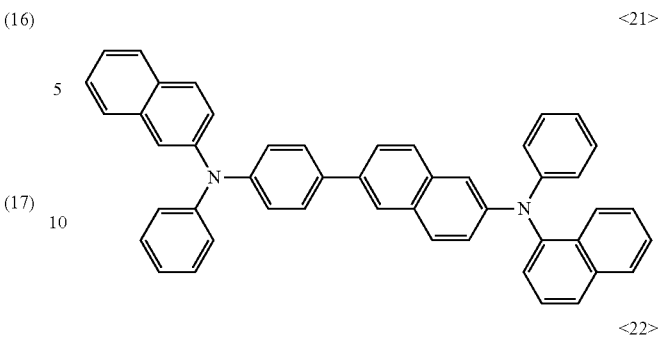

<22> 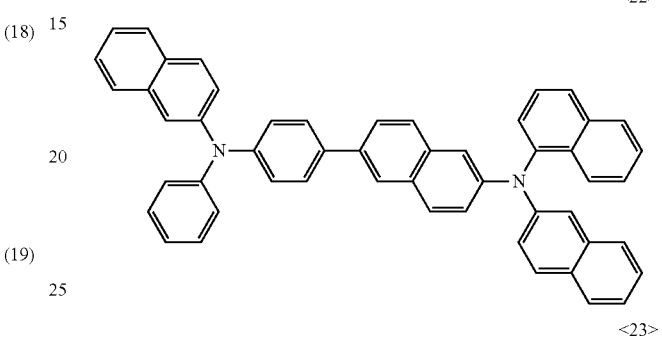

<23> 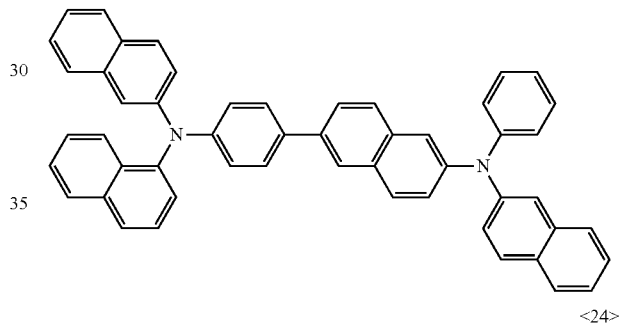

<24> 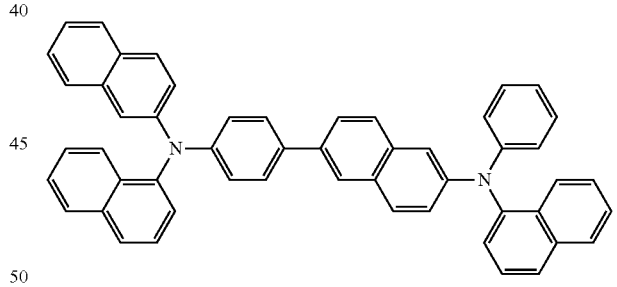

<25> 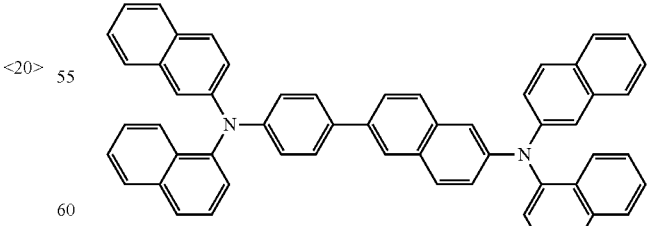

Examples of the compound represented by the formula (3) when Ar in the derivative represented by the formula (1) is pyrene include, but not limited to, the following structures represented by the formulas (26) to (63):

<Pyrene Derivatives>
<26>
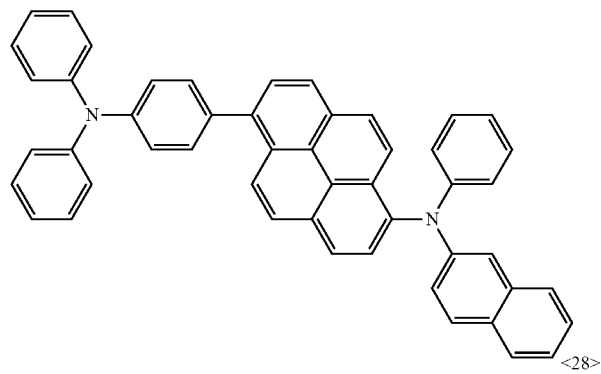
<27>
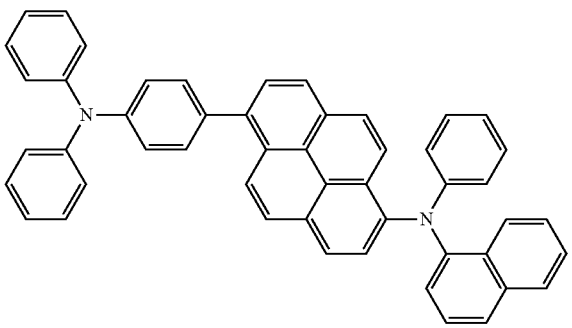
<28>
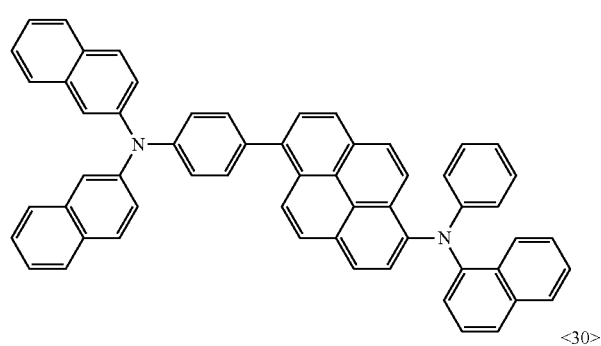
<29>
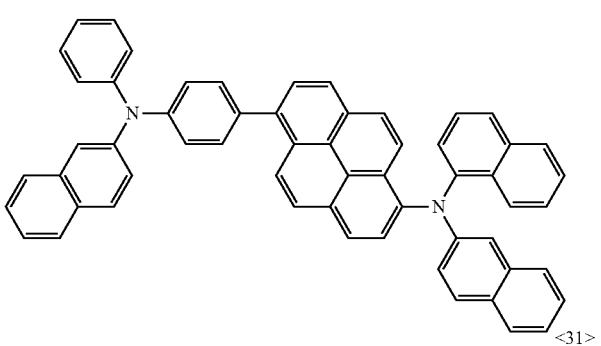
<30>
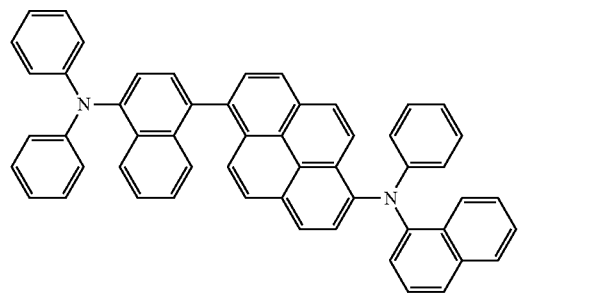
<31>
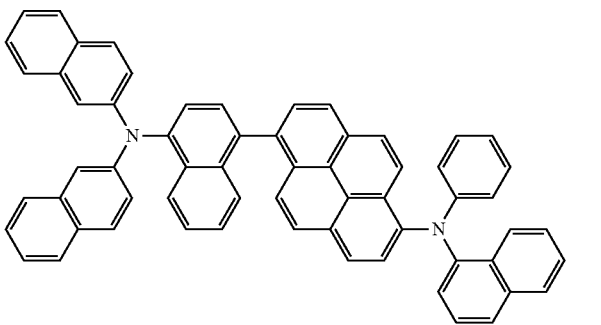
<32>
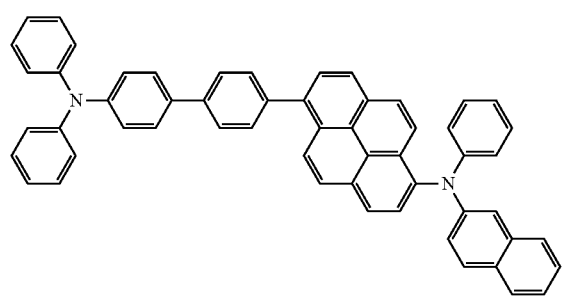
<33>
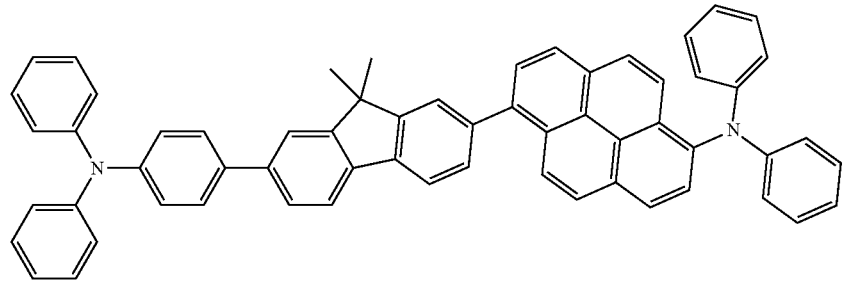

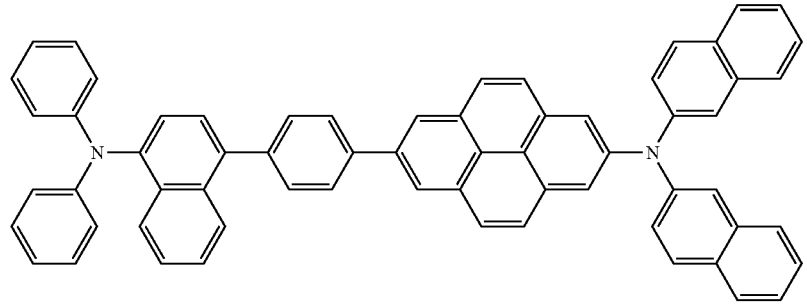
<34>
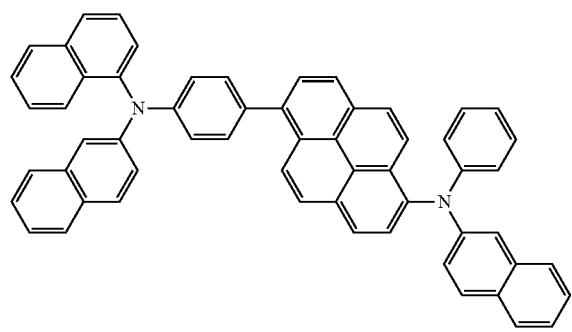
<35>
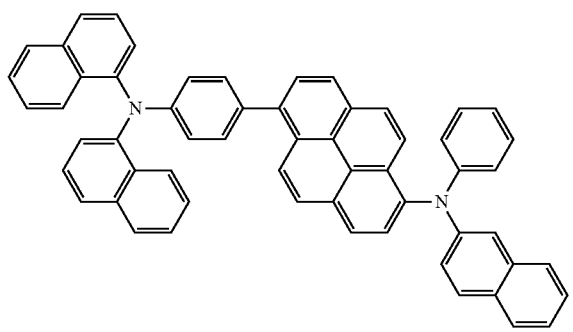
<36>
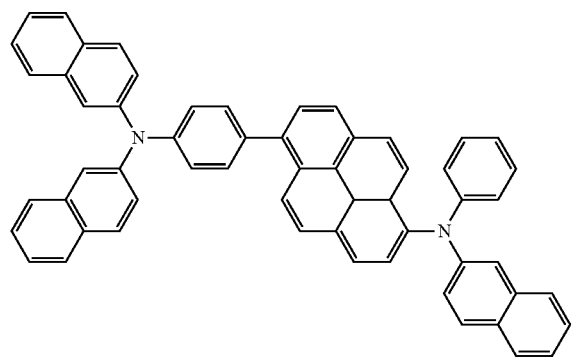
<37>
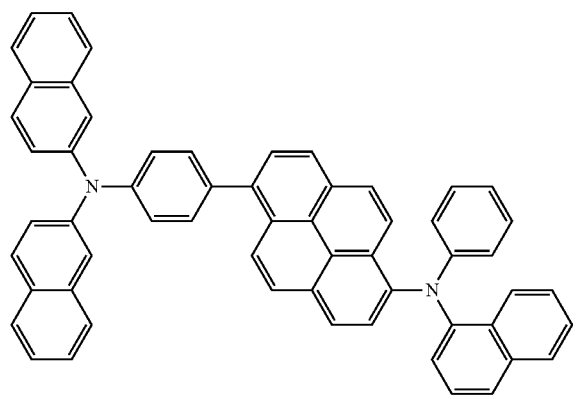
<38>
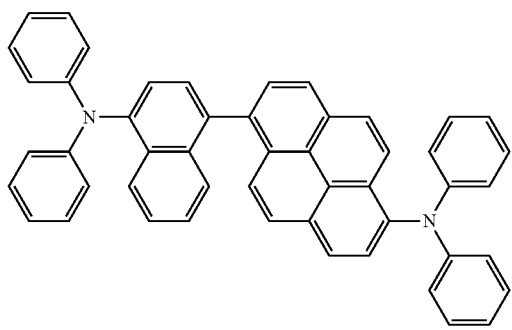
<39>

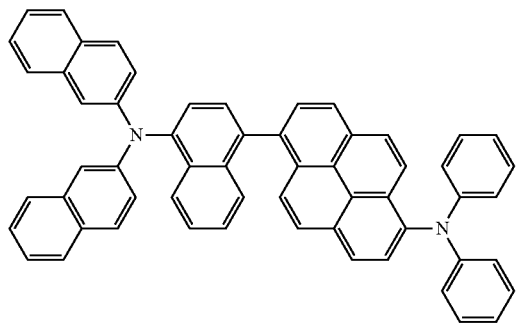
<40>
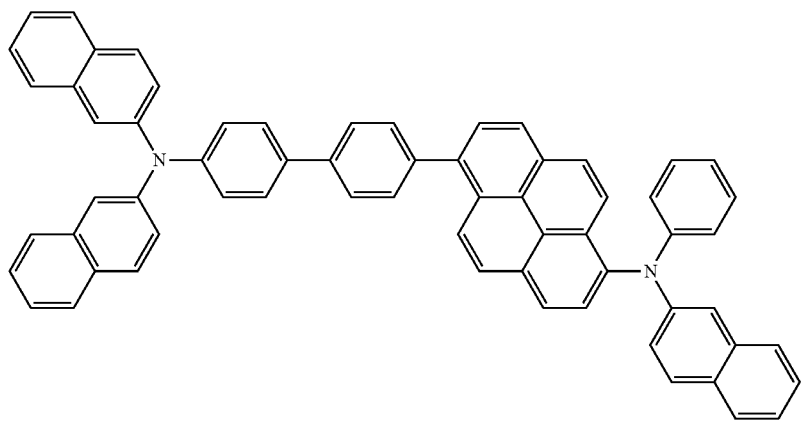
<41>
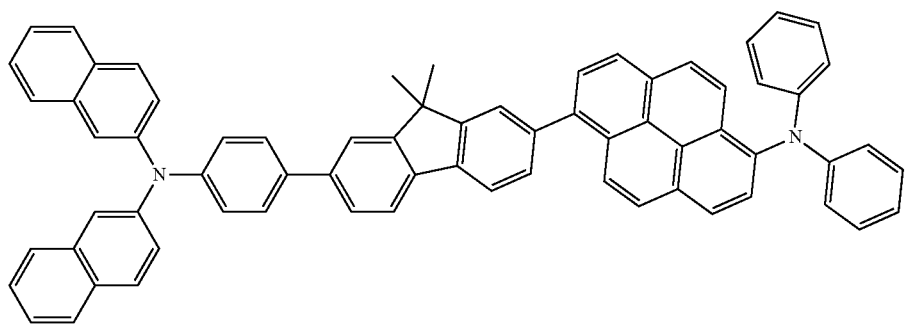
<42>
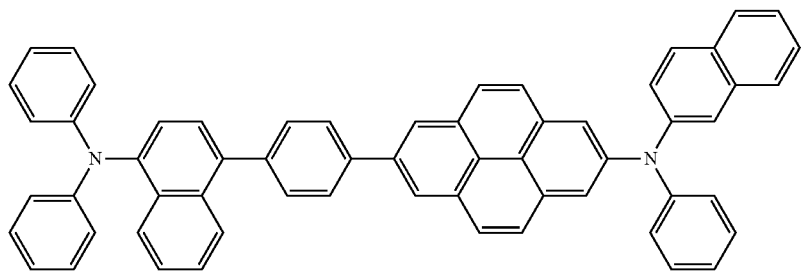
<43>

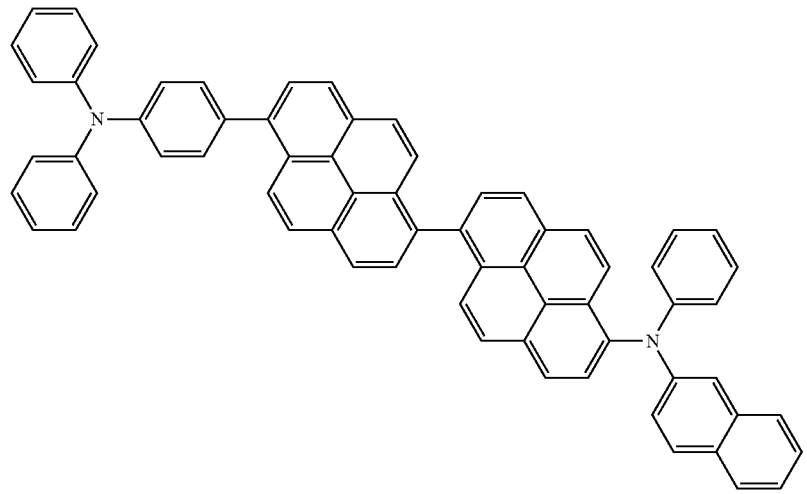
<44>
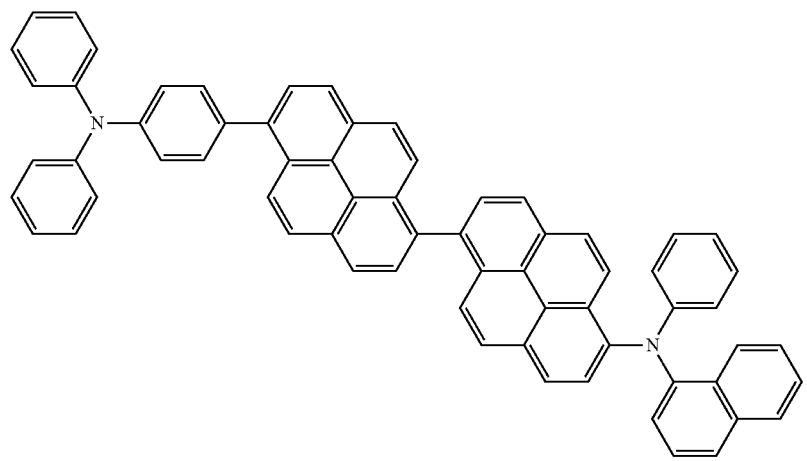
<45>
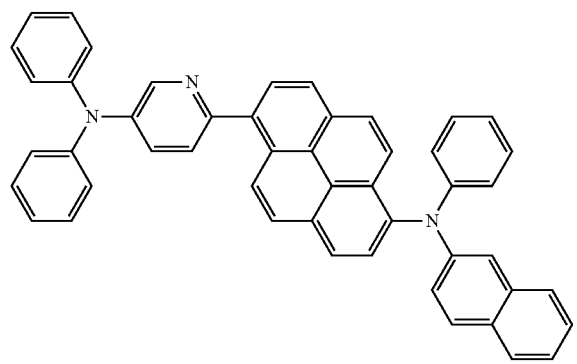
<46>
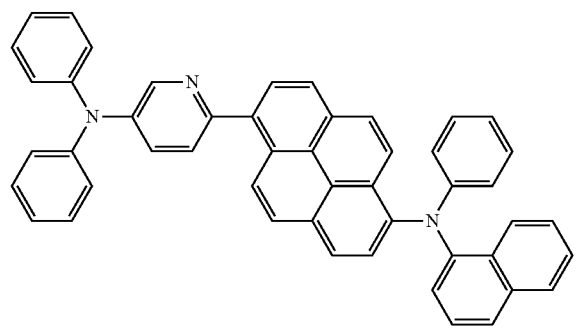
<47>

-continued
<48>
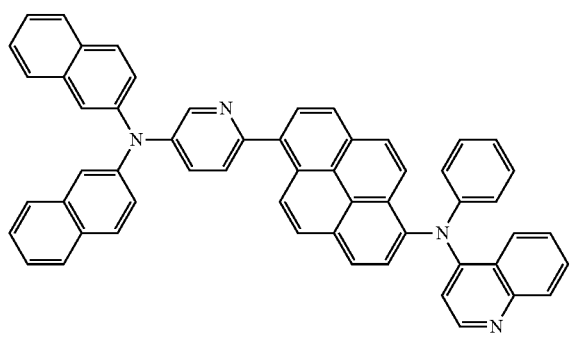
<49>
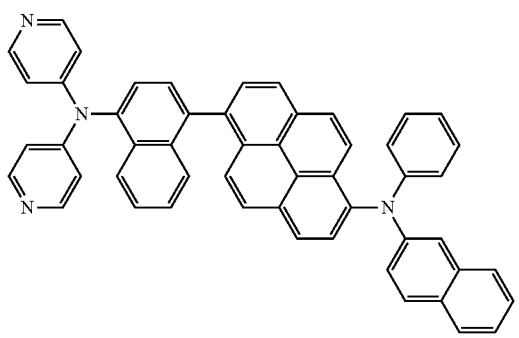
<50>
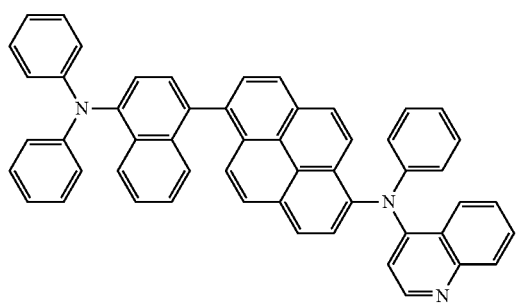
<51>
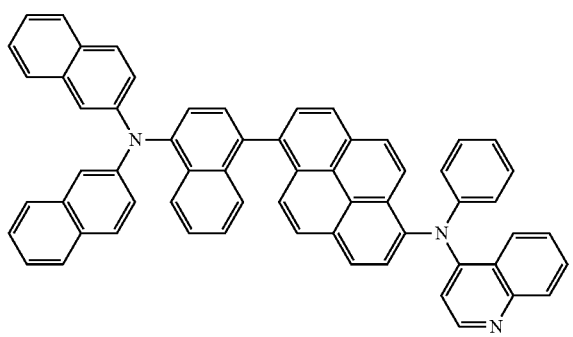
<52>
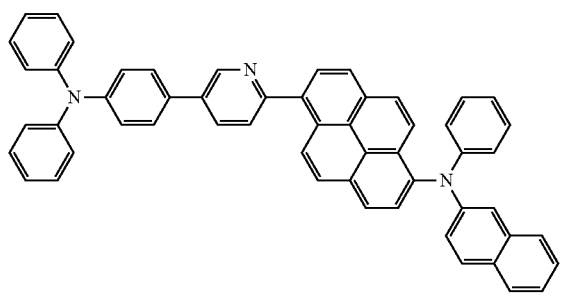
<53>
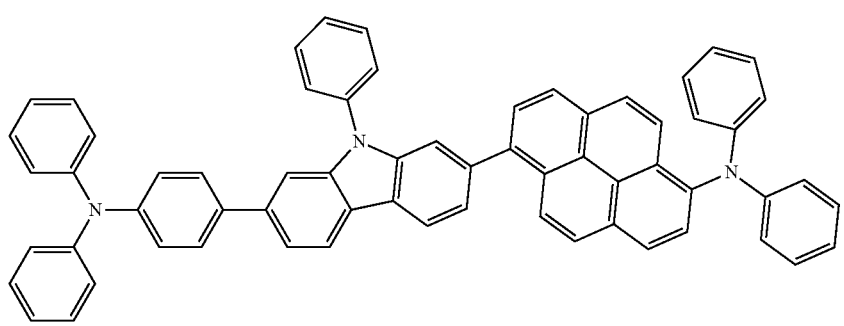
<54>
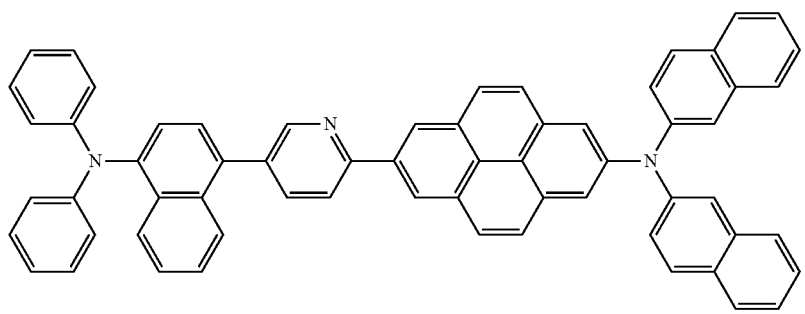

-continued
<55>
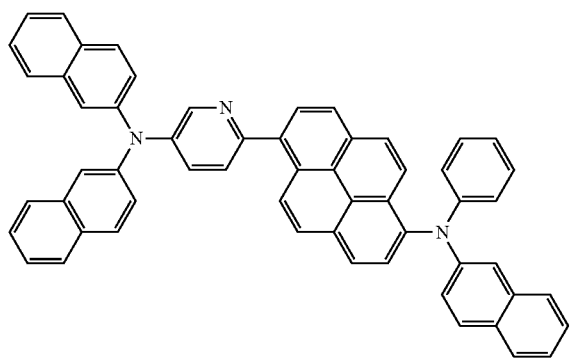
<56>
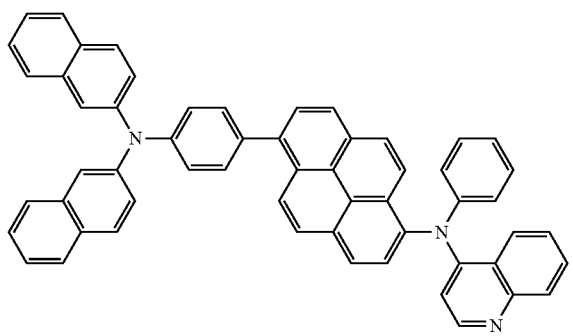
<57>
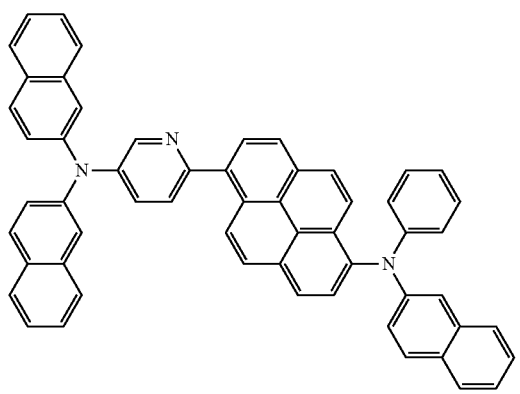
<58>
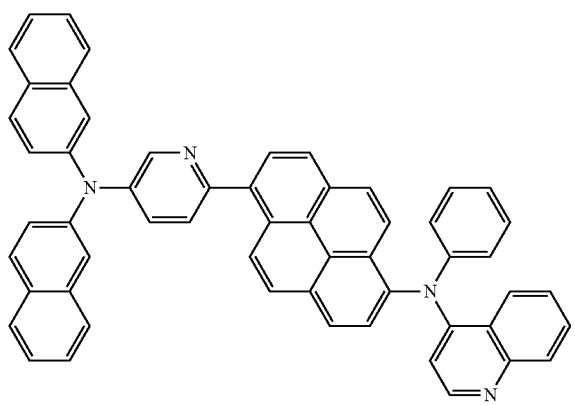
<59>
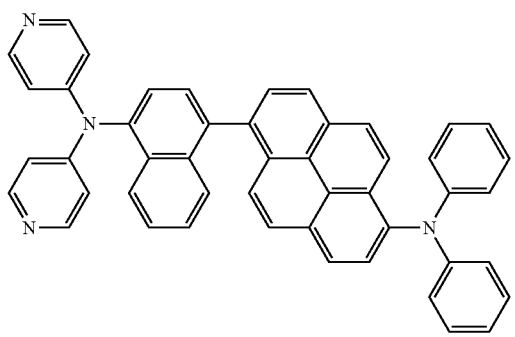
<60>
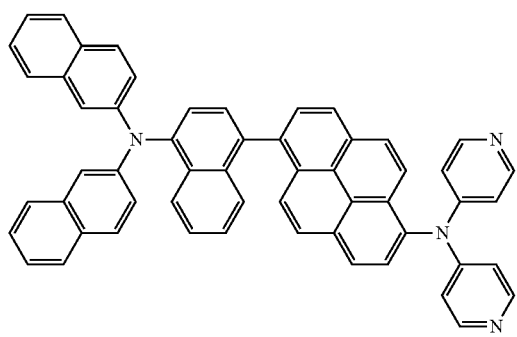

-continued

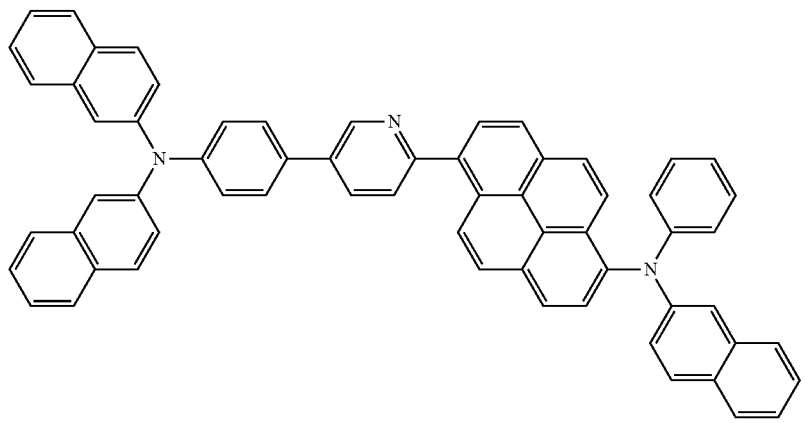
<61>

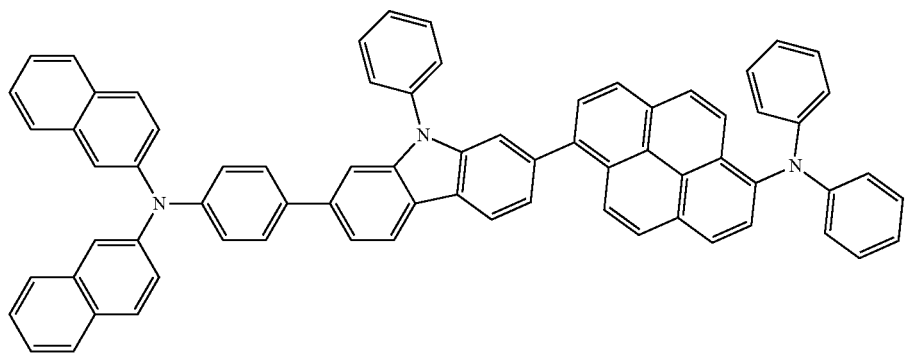
<62>

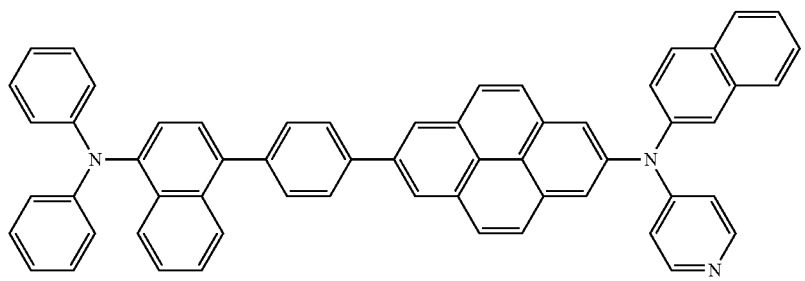
<63>

In a manufacturing method of an asymmetric arylamine derivative for an organic electroluminescent element, represented by the formula (1) with the proviso that the arylamine derivative does not include a symmetrical axis and a symmetrical surface in a molecule:

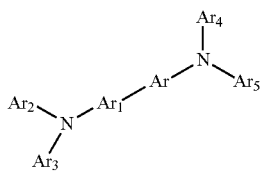
(1)

wherein Ar represents a $C_{10}$-$C_{20}$ divalent aryl group, $Ar_1$ is a divalent $C_6$-$C_{30}$ aryl group, and $Ar_2$ to $Ar_5$ each independently represents a divalent $C_6$-$C_{30}$ aryl group, at least one of $Ar_2$ to $Ar_5$ having a different structure when the secondary amine and the tertiary amine in Ar are substituted at symmetrical positions, and $Ar_2$ to $Ar_5$ having the same structure or different structures when the secondary amine and the tertiary amine in Ar are substituted at asymmetrical positions, the aryamine derivative may be prepared by sequentially substituting the functional groups with a secondary amine and a tertiary amine by subjecting a starting material, an aryl compound (Ar) core di-substituted with the same functional group or different functional groups to a well known process such as an aryl amination reaction or a Suzuki-coupling reaction, as represented by the following reaction scheme 1:

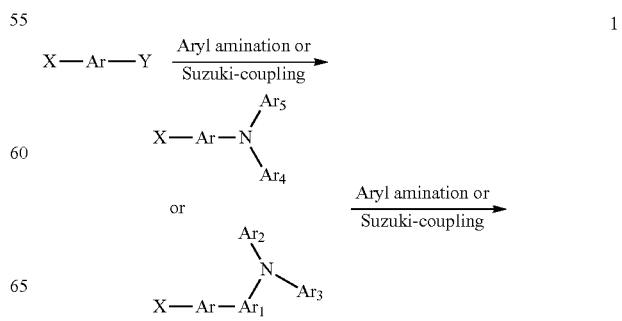
1

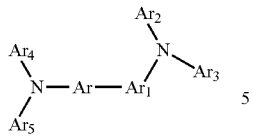

wherein X and Y represent the same group or different groups enabling an aryl amination reaction, $Ar_1$ is a divalent $C_6$-$C_{30}$ aryl group, and $Ar_2$ to $Ar_5$ each independently represents a divalent $C_6$-$C_{30}$ aryl group, at least one of $Ar_2$ to $Ar_5$ having a different structure when the secondary amine and the tertiary amine in Ar are substituted at symmetrical positions, and $Ar_2$ to $Ar_5$ having the same structure or different structures when the secondary amine and the tertiary amine in Ar are substituted at asymmetrical positions.

In the reaction scheme 1, Ar is preferably selected from the group consisting of naphthalene, pyrene, perylene and pentacene and is more preferably naphthalene represented by the reaction scheme 2, or pyrene represented by the reaction scheme 3:

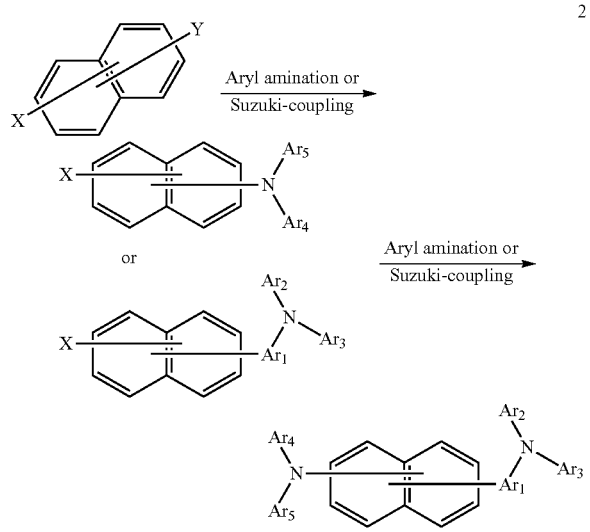

wherein X, Y, and Ar1 to $Ar_5$ are the same as defined in the reaction scheme 1; and

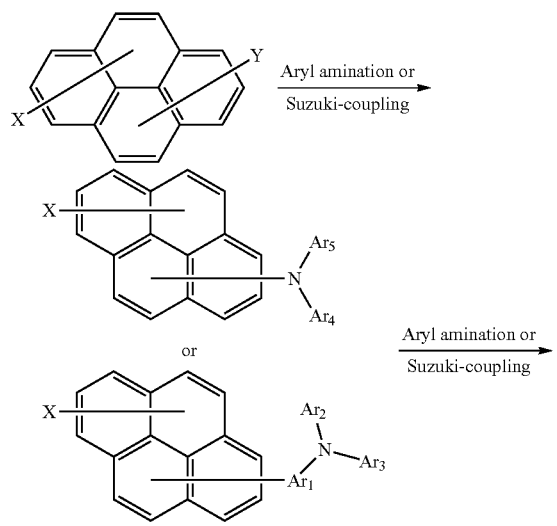

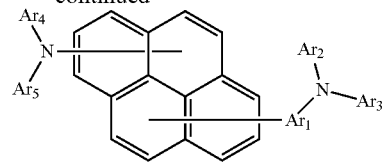

wherein X, Y, and $Ar_1$ to $Ar_5$ are the same as defined in the reaction scheme 1.

In the reaction scheme 1, X and Y are preferably selected from the group consisting of a halogen, amine and hydroxyl group, but not limited thereto. Within the scope of the present invention, there is no special limitation on the functional group as long as different substituent groups can be induced through sequential reactions.

More specifically, the arylamine derivative represented by the formula (1) can be easily prepared by sequentially substituting the functional groups with a secondary amine and a tertiary amine by reacting a starting material, an aryl compound di-substituted with the same functional group or different functional groups, for example, an aryl compound core having the same halogen or different halogens, halogen and amine, or halogen and hydroxyl group, with arylamine or boronic acid of arylamine.

There have been numerous reports about aryl-aryl coupling reactions between arylamines and aryl halogen compounds for inducing secondary amine and tertiary amine to provide for an arylamine compound core di-substituted with the same group or different groups, and the asymmetric arylamine pyrene derivative represented by the formula (1) can be easily prepared under reaction conditions described in these reports. In particular, known are a coupling reaction using copper (Cu) (Canadian Journal Chemistry, 61, 1983, 86-91), a reaction using t-BuOK (Organic Letters, 5, 19, 2003, 3515-3518), a reaction using a nickel catalyst (Organic Letters, 7, 11, 2005, 2209-2211), a reaction using a palladium catalyst (Journal of Organic Chemistry, 64, 15, 1999, 5575-5580), and so on.

So far, many reports on Suzuki coupling reaction for inducing an amino group by an esterification of boronic acid have been published (Chem. Rev. Vol. 95, No. 7, 2457 (1995), etc.), and the Suzuki-coupling reaction may be carried out in the reaction conditions described therein. The reaction is carried out generally at normal pressure in inert gas atmosphere such as nitrogen, argon, helium and the like, and also under pressurized condition as, appropriated. The reaction temperature is in the range of from 15 to 300° C. preferably from 30 to 200° C.

The esterification of boronic acid according to the present invention may be carried out in accordance with known methods (Japan Chemical Society' editorial, The Experimental Chemistry Course No. 4 edition, Vol 24, 61-90; J. Org. Chem., Vol. 60, 7508 (1995), etc.).

Examples of the arylamine useful to synthesize the asymmetric arylamine derivative represented by the formula (1) by inducing different substituent groups to a pyrene compound di-substituted with the same group or different groups may include, but not limited to, the following compounds represented by the formulae (64) to (69) and examples of the arylboronic acid may include, but not limited to, the following compounds represented by the formulae (70) to (74):

<Arylamines>

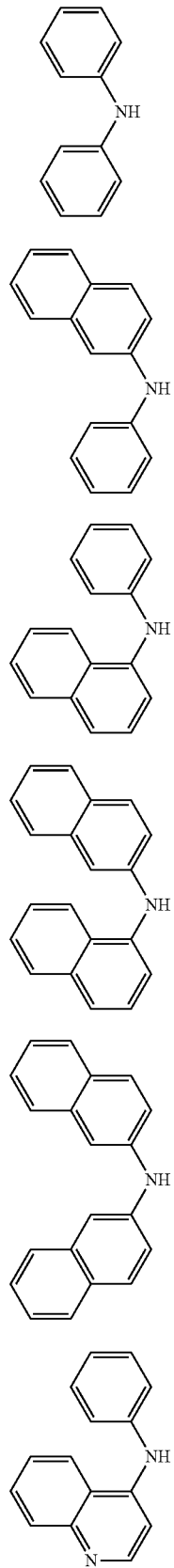

<Arylboronic Acids>

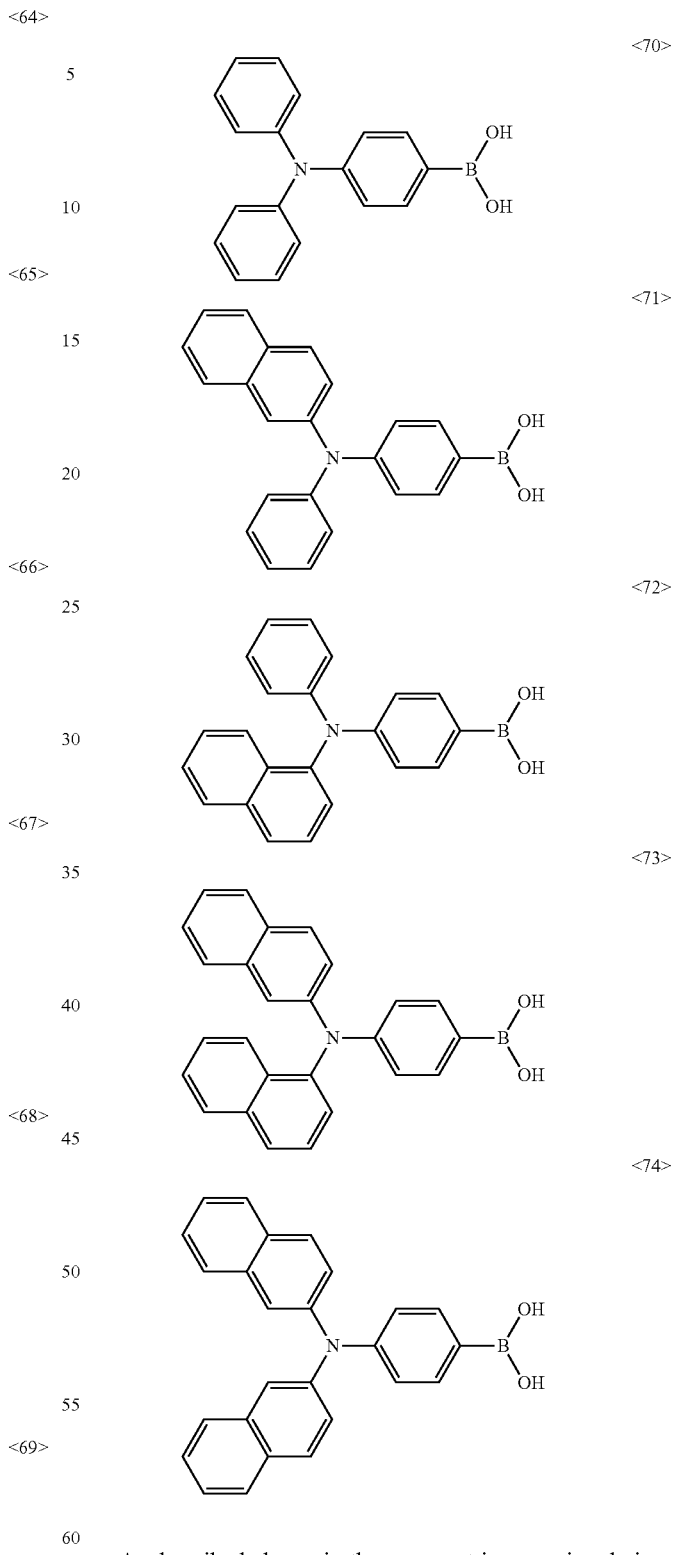

As described above, in the asymmetric aryamine derivatives represented by the formula (1) according to the present invention, which do not include a symmetrical axis and a symmetrical surface in a molecule by sequentially inducing a secondary amine and a tertiary amine to an aryl compound Ar core, when they are employed to organic EL elements, excellent blue color purity, remarkably improved efficiency of blue light emission and long lifetime can be achieved, compared to the conventional aryamine derivative structure having the same secondary or tertiary amine induced thereto.

Hereinafter, an organic thin layer material for an organic EL element according to the present invention and the organic EL element using the same will be described.

The present invention provides an organic thin layer material for an organic EL element including the asymmetric aryamine derivative represented by the formula (1). Any organic thin layer material for an organic EL element can be suitably applied to the present invention as long as it contains the asymmetric aryamine derivative represented by the formula (1).

According to the present invention, the organic thin layer material including the asymmetric aryamine derivative represented by the formula (1) is preferably a light-emitting material or a dopant material.

Since the organic thin layer material for an organic EL element, exclusive of the asymmetric aryamine derivative represented by the formula (1), are well known in the art, a detailed description thereof will be omitted. However, the organic thin layer material will be briefly described by way of example in describing the organic EL element.

In the organic EL element according to the present invention, including an anode, a cathode and a plurality of organic thin layers positioned between the anode and the cathode, an organic thin layer material is included in at least one of the organic thin layers.

The organic thin layers may include at least one selected from a hole injection layer, a hole transport layer, a light-emitting layer, an electron injection layer and an electron transport layer. Preferably, the organic thin layers including the organic thin layer material for an organic EL element may be a light-emitting layer.

The organic EL element according to the present invention will now be described in detail with a specific example.

FIG. 1 is a schematic diagram illustrating a structure of an organic electroluminescent (EL) element according to an embodiment of the present invention. As shown in FIG. 1, the organic EL element according to the present invention may include a substrate 1, an anode 2, a hole transport layer 4, a light-emitting layer 5, an electron transport layer 6, and a cathode 7. An electron injection layer (not shown) may further be provided between the electron transport layer 6 and the cathode 7, and a hole injection layer 3 may further be provided between the anode 2 and the hole transport layer 4.

Here, the organic thin layers may include the hole injection layer 3, the hole transport layer 4, the light-emitting layer 5, the electron transport layer 6, and an electron injection layer (not shown), and so on, which may be disposed between the anode 2 and the cathode 7, and all or part of these layers may contain an organic thin layer material including the asymmetric aryamine derivative represented by the formula (1).

Examples of the anode 2 may include metal oxides or nitrides such as ITO, IZO, tin oxide, zinc oxide, zinc aluminum oxide, or titanium nitride, metals such as gold, platinum, silver, copper, aluminum, nickel, cobalt, lead, molybdenum, tungsten, tantalum, or niobium, metal alloys of these metals, alloys of copper iodide; conductive polymers such as polyaniline, polythiopyne, polypyrole, polyphenylenevinylene, poly(3-methylthiopyne), or polyphenylene sulfide, and so on. The anode 2 may be formed of a single material of the listed materials or a mixture of two or more of the listed materials. In addition, the anode 2 may have a multi-layered structure including a plurality of layers of the same composition or different compositions.

The hole injection layer 3 of the present invention may be formed of not only the aryamine derivative represented by the formula (1) but also organic thin film materials known in the art, non-limiting examples of which may include PEDOT/PSS or copper phthalocyanine (CuPc), 4,4',4"-tris(3-methylphenylphenylamino)triphenylamine (m-MTDATA), 4,4',4"-tris(N-(2-naphthyl)-N-phenyl-amino)-triphenylamine (2-TNATA), and so on, to a thickness of 5 nm to 40 nm.

The hole transport layer 4 of the present invention may be formed of not only the aryamine derivative represented by the formula (1) but also organic thin film materials known in the art, non-limiting examples of which include 4,4'-bis[N-(1-naphthyl)-N-phenyl-amino]-biphenyl (NPD) or N,N'-diphenyl-N,N'-bis(3-methylphenyl)-1,1'-biphenyl-4,4'-diamine (TPD)), and so on.

The light-emitting layer 5 of the present invention may be formed of not only the aryamine derivative represented by the formula (1) but also fluorescent or phosphorescent host and dopant materials known in the art. Here, the aryamine derivative represented by the formula (1) may be added in an amount within a generally added amount range of the general fluorescent or phosphorescent dopant.

Non-limiting examples of the host materials for the light-emitting layer may include 4,4'-N,N-dicarbazolebiphenyl (CBP), 1,3-N,N-dicarbazolebenzene (mCP), and derivatives thereof. In addition, it has recently been known that BAlq capable of transporting electrons or Al complexes of the similar type to the BAlq are useful as phosphorescent host materials, and specific examples thereof may include 4,4'-bis (2,2-diphenyl-ethen-1-yl)diphenyl (DPVBi), bis(styryl) amines (DSA), bis(2-methyl-8-quinolinolato)(triphenylsiloxy)aluminum (III) (SAlq), bis(2-methyl-8-quinolinolato) (para-phenolato)aluminum (III) (BAlq), bis(salen) zinc (II), 1,3-bis[4-(N,N-dimethylamino)phenyl-1,3,4-oxadiazolyl] benzene (OXD8), 3-(biphenyl-4-yl)-5-(4-dimethylamino)-4-(4-ethylphenyl)-1,2,4-triazole (p-EtTAZ), 3-(4-biphenyl)-4-phenyl-5-(4-tertiary-butylphenyl)-1,2,4-triazole (TAZ), 2,2', 7,7'-tetrakis(biphenyl-4-yl)-9,9'-spirofluoroene (Spiro-DPVBI), tris(para-terphenyl-4-yl)amine (p-TTA), 5,5-bis (dimesitylboryl)-2,2-bithiophene (BMB-2T), perylene, and so on.

In addition, usable examples of the host or dopant materials may include tris(8-quinolinato)aluminum (III) (Alq3), DCM1 (4-dicyanomethylene-2-methyl-6-(para-dimethylaminostyryl)-4H-pyrane), DCM2 (4-dicyanomethylene-2-methyl-6-(julolidin-4-yl-vinyl)-4H-pyrane), DCJT (4-(dicyanomethylene)-2-methyl-6-(1,1,7,7-tetramethyl julolidyl-9-enyl)-4H-pyrane), DCJTB (4-(dicyanomethylene)-2-tertiarybutyl-6-(1,1,7,7-tetramethyl julolidyl-9-enyl)-4H-pyrane), DCJTI (4-dicyanomethylene)-2-isopropyl-6-(1,1,7, 7-tetramethyl julolidyl-9-enyl)-4H-pyrane), Nile red, Rubrene, and so on.

The listed host and dopant materials may be added singly or in combination of two or more of the materials listed above.

The electron transport layer 6 may include not only the asymmetric aryamine derivative represented by the formula (1) but also aryl substituted oxadiazole, aryl-substituted triazole, aryl-substituted phenanthroline, benzoxazole or benzcyazole compounds. Examples of the electron transport layer 6 may include 1,3-bis(N,N-t-butyl-phenyl)-1,3,4-oxadiazole (OXD-7); 3-phenyl-4-(1'-naphthyl)-5-phenyl-1,2,4-triazole (TAZ); 2,9-dimethyl-4,7-diphenyl-phenanthroline (BCP); bis(2-(2-hydroxyphenyl)-benzoxazolate)zinc; or bis (2-(2-hydroxyphenyl)-benzcyazolate)zinc. Useful examples of an electron transporting material may include a compound selected from (4-biphenyl)(4-t-butylphenyl)oxydiazole (PDB) and tris(8-quinolinato)aluminum (III) (Alq3). Preferably, the electron transporting material may be tris(8-quinolinato)aluminum (III) (Alq3).

The electron injection layer and the cathode 7 may be formed of materials known in the art, and non-limiting examples thereof may include LiF and a metal having a low work function such as Al, Ca, Mg, or Ag, respectively. Al is preferably used for the cathode 7.

The organic EL element according to the present invention may be employed to a display device. The display device may be a display device using a backlight unit. The organic EL element may be used as a light source of a backlight unit or as an independent light source. The display device may be an organic light emitting display (OLED).

Hereinafter, examples of the present invention will be described. However, the present invention is not limited by these examples. In particular, although the synthesis examples illustrate synthesis methods of some compounds, other compounds may also be synthesized by one skilled in the art using the same synthesis methods. Thus, the asymmetric aryamine derivative which does not include a symmetrical axis and a symmetrical surface in a molecule can be synthesized by the inventive methods or well known methods. However, the present invention is not limited to the methods illustrated herein.

SYNTHESIS EXAMPLE 1

Synthesis of Compound of Formula 22

The overall synthesis process is shown in the reaction scheme 4.

First, 5.00 g (15.0 mmol) of 6-bromo-1-iodo-naphthalene, 4.33 g (12.8 mmol) of 4-(naphthalene-2-yl-phenyl-amino)-phenylboronic acid and a catalytic amount of tetrakis(triphenylphosphine)-palladium were placed into a 250 mL-3-neck flask under a nitrogen atmosphere, 60 mL of 1,2-dimethoxy ethane and 30 mL of 2M-sodium carbonate aqueous solution were added thereto, followed by refluxing at 95° C. for 18 hours. After the reaction was completed, the reaction mixture was cooled to the room temperature, and a formed organic layer was extracted using distilled water and ethylacetate, dried with magnesium sulfate to then remove a solvent under reduced pressure. The resultant product was reprecipitated using tetrahydrofuran and methanol for filtration, followed by vacuum drying, and 8.18 g of the target compound [4-(6-bromo-naphthalene-2-yl)-phenyl]-naphthalene-2-yl-phenyl-amine represented by the formula 75 was obtained (yield: 64%), as confirmed by (MS)(EI) calcd for $C_{32}H_{22}BrN$, 500.43; Found: 499.

Under the nitrogen atmosphere, 4.00 g (8.0 mmol) of [4-(6-bromo-naphthalene-2-yl)-phenyl]-naphthalene-2-yl-phenyl-amine represented by the formula 75, 2.48 g (9.2 mmol) of naphthalene-2-yl-naphthalene-1-yl-amine, catalytic amounts of bis(dibenzylidene acetone)-palladium, tri-t-butylphosphine, and sodium-t-butoxide were placed into a 250 mL-3-neck flask, 80 mL of toluene was added thereto, followed by stirring at room temperature for 5 hours. After the reaction was completed, the reaction mixture was cooled to the room temperature, and a formed organic layer was extracted using distilled water and ethylacetate, dried with magnesium sulfate to then remove a solvent under reduced pressure. The resultant product was reprecipitated using tetrahydrofuran and methanol for filtration, followed by vacuum drying, and 4.35 g of the target compound, 6-[(4-(naphthalene-2-yl-phenyl-amino)-phenyl]-naphthalene-2-yl-naphthalene-2yl-naphthalene-1-yl-amine (yield: 79%), as confirmed by MS (EI) calcd for $C_{52}H_{36}N_2$, 688.86; Found: 688.

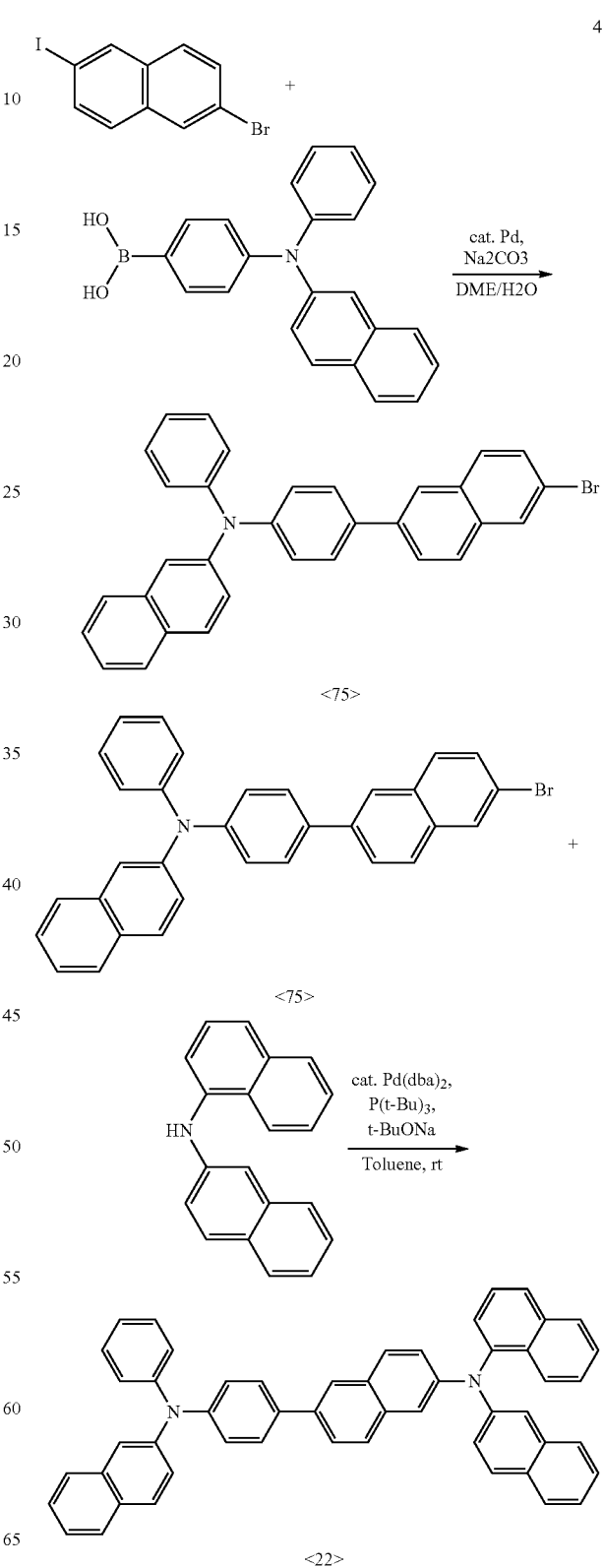

SYNTHESIS EXAMPLE 2

Synthesis of Compound of Formula 23

The overall synthesis process is shown in the reaction scheme 5. As represented by the reaction scheme 5, the same procedure as in Synthesis Example 1 was conducted, except that [4-(6-bromo-naphthalene-2-yl)-phenyl]-naphthalene-1-yl-naphthalene-2-yl-amine represented by the formula 76 was synthesized using naphthalene-2-yl-naphthalene-1-yl-phenylboronic acid, instead of naphthalene-2-yl-phenyl-amine in the Suzuki-coupling reaction in Synthesis Example 1, and naphthalene-2-yl-phenyl amine, instead of naphthalene-2-yl-naphthalene-1-yl-amine of Synthesis Example 1, was used in an arylamination reaction. The target compound, 6-[(4-(naphthalene-2-yl-naphthalene-1-amino)-phenyl]-naphthalene-2-yl-naphthalene-2-yl-phenyl-amine, represented by the formula 23 was obtained, as confirmed by MS (EI) calcd for $C_{52}H_{36}N_2$, 688.86; Found: 688.

+

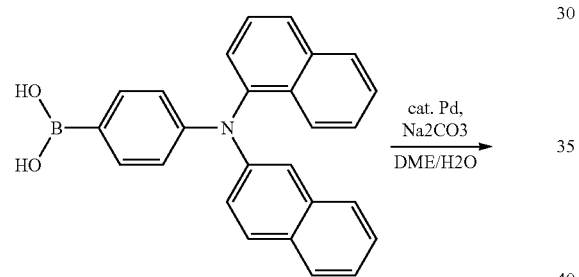

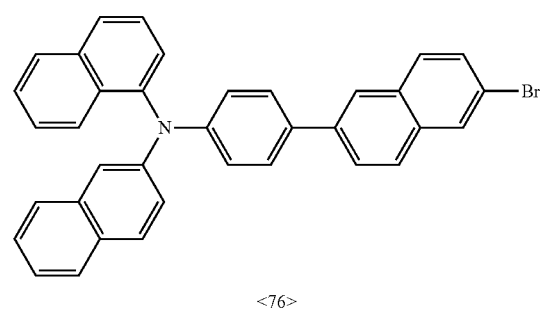

+

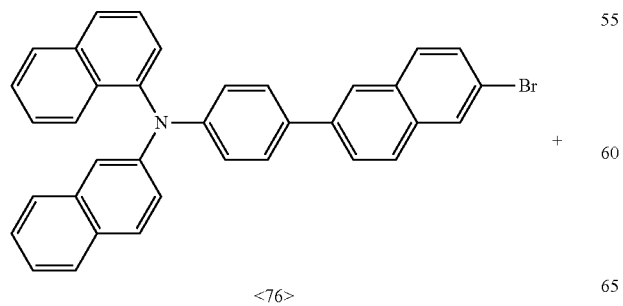

<76>

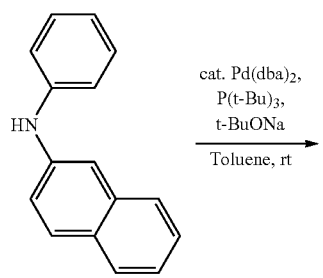

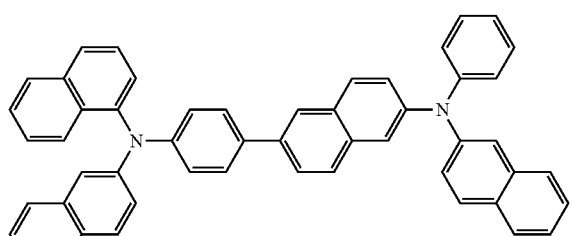

<23>

SYNTHESIS EXAMPLE 3

Synthesis of Compound of Formula 24

The overall synthesis process is shown in the reaction scheme 6. As represented by the reaction scheme 6, the same procedure as in Synthesis Example 2 was conducted, except that naphthalene-1-yl-phenyl amine was used for an arylamination reaction, instead of naphthalene-2-yl-naphthalene-1-yl-amine in SYNTHESIS EXAMPLE 2. The target compound, 6-[(4-(naphthalene-2-yl-naphthalene-1-amino)-phenyl]-naphthalene-2-yl-naphthalene-1-yl-phenyl-amine, represented by the formula 24 was obtained, as confirmed by MS (EI) calcd for $C_{52}H_{36}N_2$, 688.86; Found: 688.

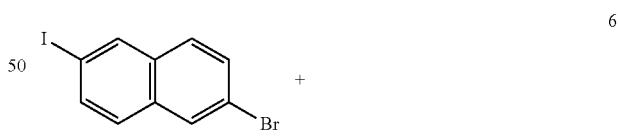

+

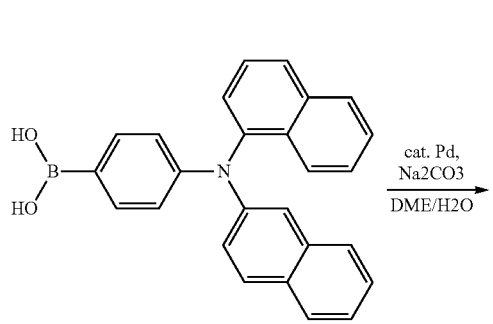

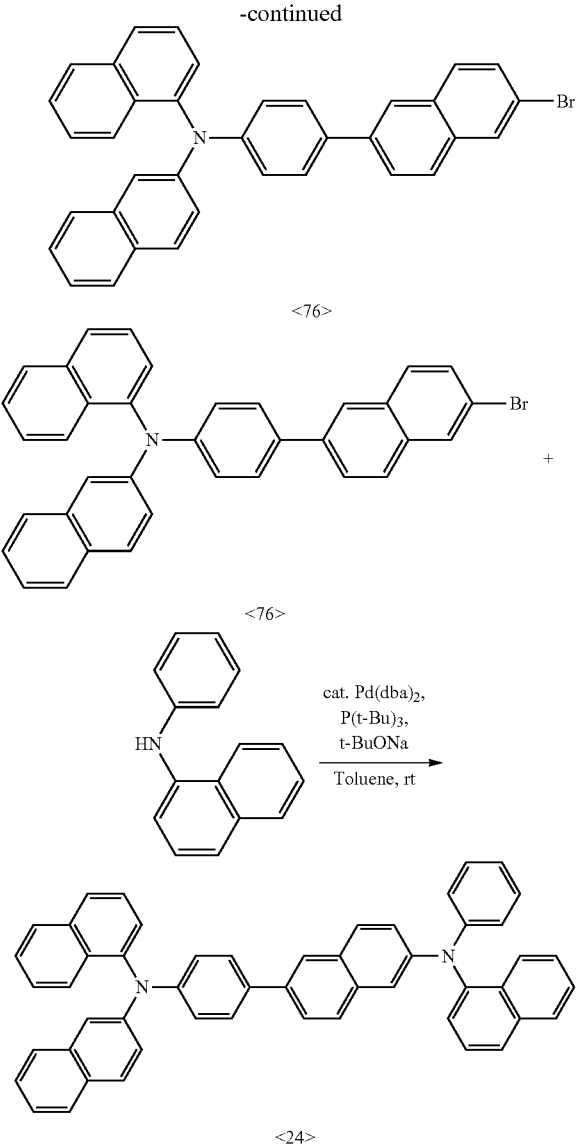

<76>

<76>

<24>

SYNTHESIS EXAMPLE 4

Synthesis of Compound of Formula 29

The overall synthesis process is shown in the reaction scheme 7.

First, 45.0 mmol of 1,6-dibromopyrene, 12.8 mmol of 4-(naphthalene-2-yl-phenyl-amino)-phenylboronic acid and a catalytic amount of tetrakis(triphenylphosphine)-palladium were placed into a 500 mL-3-neck flask under a nitrogen atmosphere, 225 mL of 1,2-dimethoxy ethane and 60 mL of 2M-sodium carbonate aqueous solution were added thereto, followed by refluxing at 95° C. for 18 hours. After the reaction was completed, the reaction mixture was cooled to the room temperature, an excess of dibromopyrene was collected by filtration, and a formed organic layer was extracted using distilled water and ethylacetate, dried with magnesium sulfate to then remove a solvent under reduced pressure. The resultant product was reprecipitated using tetrahydrofuran and methanol for filtration, followed by vacuum drying, and the target compound [4-(6-bromo-pyrene-1-yl)-phenyl]-naphthalene-2-yl-phenyl-amine represented by the formula 77 was obtained (yield: 84%), as confirmed by MS (EI) calcd for $C_{38}H_{24}BrN$, 574.51; Found: 574.

Under the nitrogen atmosphere, 8.0 mmol of [4-(6-bromo-naphthalene-2-yl)-phenyl]-naphthalene-2-yl-phenyl-amine represented by the formula 77, 9.2 mmol of naphthalene-2-yl-naphthalene-1-yl-amine, a catalytic amount of bis(dibenzylidene acetone)-palladium, tri-t-butylphosphine, and sodium-t-butoxide were placed into a 250 mL-3-neck flask, 80 mL of toluene was added thereto, followed by stirring at 105° C. for 5 hours. After the reaction was completed, the reaction mixture was cooled to the room temperature, and a formed organic layer was extracted using distilled water and ethylacetate, dried with magnesium sulfate to then remove a solvent under reduced pressure. The resultant product was reprecipitated using tetrahydrofuran and methanol for filtration, followed by vacuum drying, and the target compound naphthalene-2-yl-naphthalene-1-yl-{6-[4-(naphthalene-2-yl-phenyl-amino)-phenyl]-pyrene-1-yl}-amine represented by the formula 29 was obtained (yield: 79%), as confirmed by MS (EI) calcd for $C_{58}H_{38}N_2$, 762.94; Found: 762.

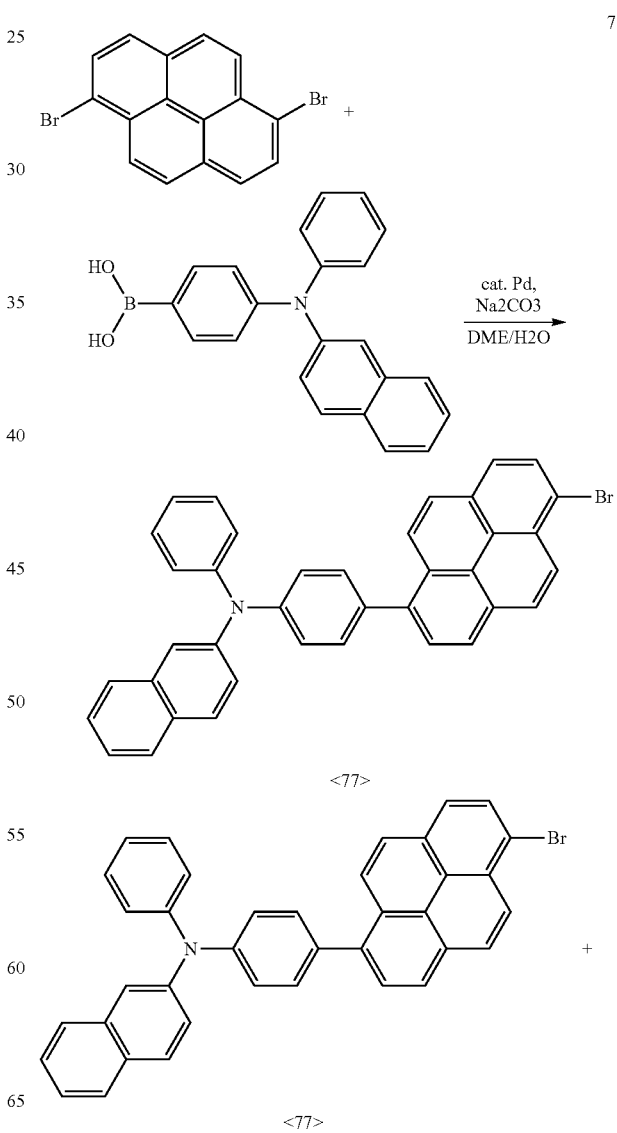

7

<77>

<77>

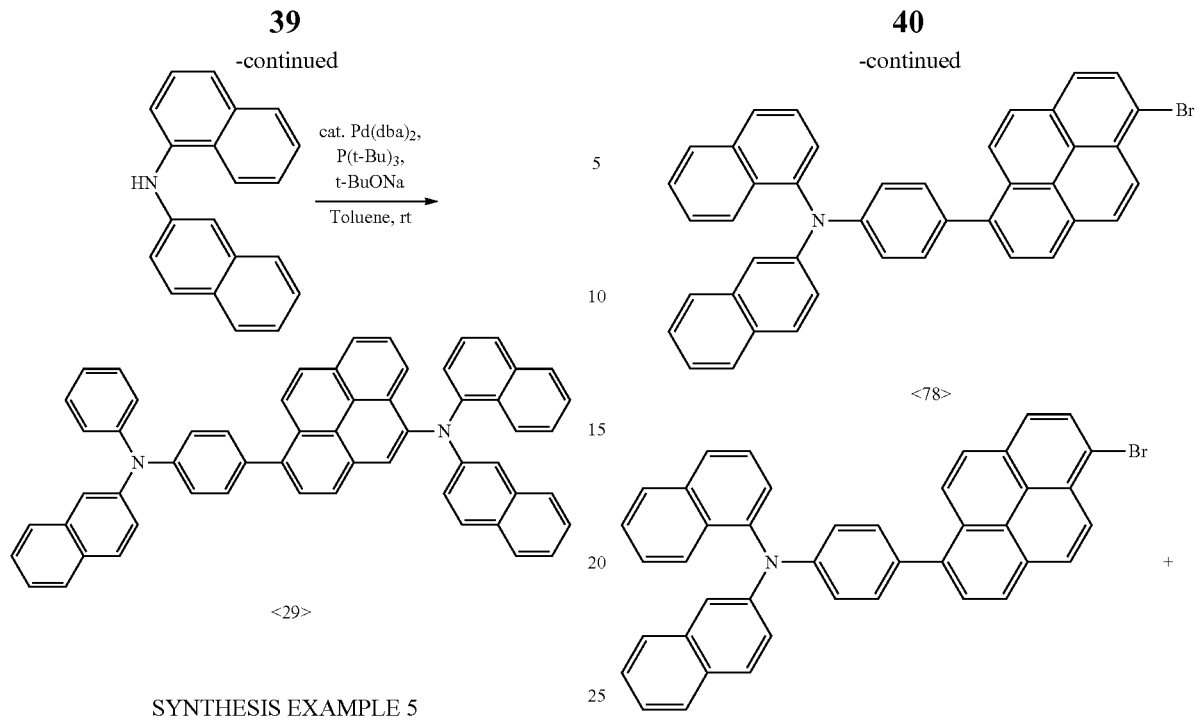

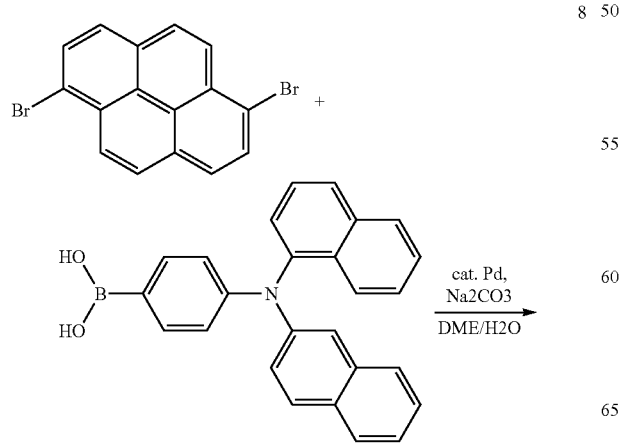

SYNTHESIS EXAMPLE 5

Synthesis of Compound of Formula 35

The overall synthesis process is shown in the reaction scheme 8. As represented by the reaction scheme 8, the same procedure as in Synthesis Example 4 was conducted, except that [4-(6-bromo-pyrene-1-yl)-phenyl]-naphthalene-1-yl-naphthalene-2-yl-amine, represented by the formula 78 was synthesized using 4-(naphthalene-1-yl-naphthalene-2-yl-amino)phenylboronic acid, instead of 4-(naphthalene-2-yl-phenyl-amino)-phenylboronic acid in the Suzuki-coupling reaction in Synthesis Example 1, and naphthalene-2-yl-phenyl amine, instead of naphthalene-2-yl-naphthalene-1-yl-amine of Synthesis Example 1, naphthalene-2-yl-phenyl amine, instead of naphthalene-1-yl-naphthalene-2-yl-amine of Synthesis Example 1, was used in an arylamination reaction. The target compound, naphthalene-2-yl-{6-[4-(naphthalene-1-yl-naphthalene-2-yl-amino)-phenyl]-pyrene-1-yl}phenyl-amine, represented by the formula 35, was obtained, as confirmed by MS (EI) calcd for $C_{58}H_{38}N_2$, 762.94; Found: 762.

SYNTHESIS EXAMPLE 6

Synthesis of Compound of Formula 36

The overall synthesis process is shown in the reaction scheme 9. As represented by the reaction scheme 9, the same procedure as in Synthesis Example 4 was conducted, except that [4-(6-bromo-pyrene-1-yl)-phenyl]-di-naphthalene-1-yl-amine, represented by the formula 79, was synthesized using 4-(di-naphthalene-1-yl-amino)-phenylboronic acid, instead of 4-(naphthalene-2-yl-phenyl-amino)-phenylboronic acid in the Suzuki-coupling reaction in Synthesis Example 1, and naphthalene-2-yl-phenyl amine, instead of naphthalene-1-yl-naphthalene-2-yl-amine of Synthesis Example 1, was used in an arylamination reaction. The target compound, {6-[4-(di-naphthalene-1-yl-amino)-phenyl]-pyrene-1-yl}-naphthalene-2-yl-phenyl-amine, represented by the formula 36, was obtained, as confirmed by MS (EI) calcd for $C_{58}H_{38}N_2$, 762.94; Found: 762.

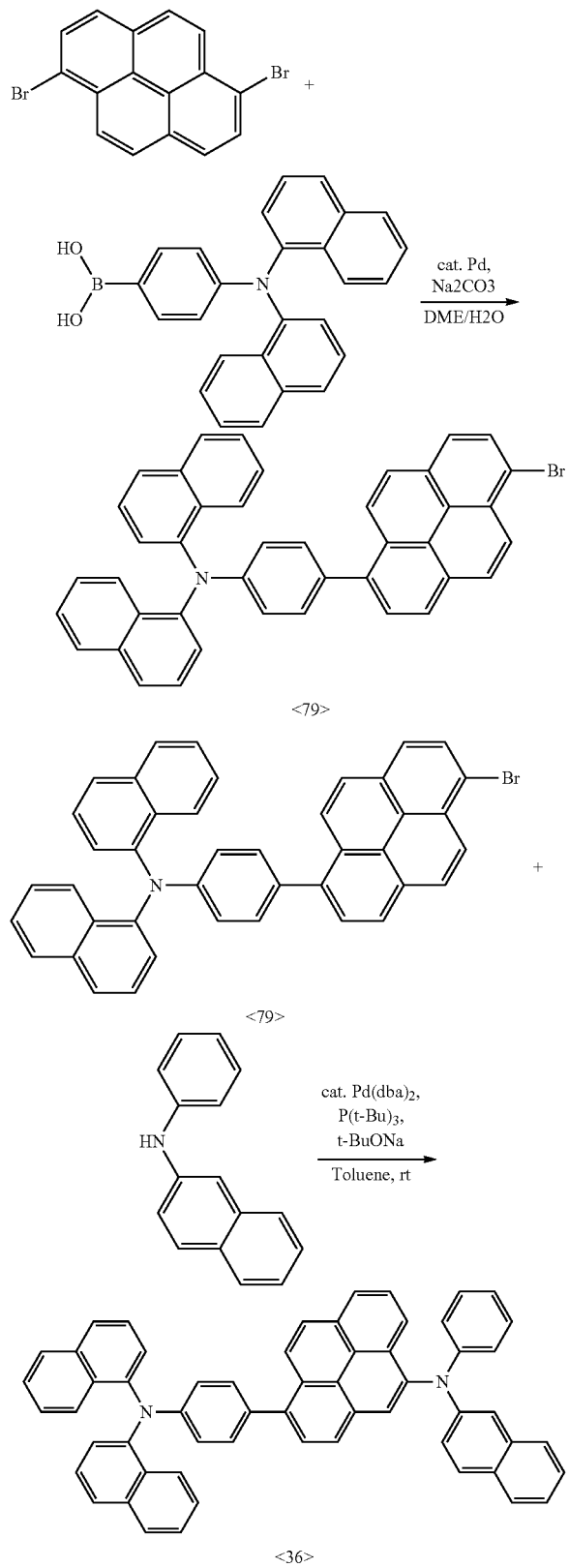

SYNTHESIS EXAMPLE 7

Synthesis of Compound of Formula 37

The overall synthesis process is shown in the reaction scheme 10. As represented by the reaction scheme 10, the same procedure as in Synthesis Example 1 was conducted, except that [4-(6-bromo-pyrene-1-yl)-phenyl]-di-naphthalene-2-yl-amine, represented by the formula 80, was synthesized using 4-(di-naphthalene-2-yl-amino)-phenylboronic acid, instead of 4-(naphthalene-2-yl-phenyl-amino)-phenylboronic acid, in the Suzuki-coupling reaction in Synthesis Example 1, and naphthalene-2-yl-phenyl amine, instead of naphthalene-1-yl-naphthalene-2-yl-amine of Synthesis Example 1, was used in an arylamination reaction. The target compound, {6-[4-(di-naphthalene-2-yl-amino)-phenyl]-pyrene-1-yl}-naphthalene-2-yl-phenyl-amine, represented by the formula 37, was obtained, as confirmed by MS (EI) calcd for $C_{58}H_{38}N_2$, 762.94; Found: 762.

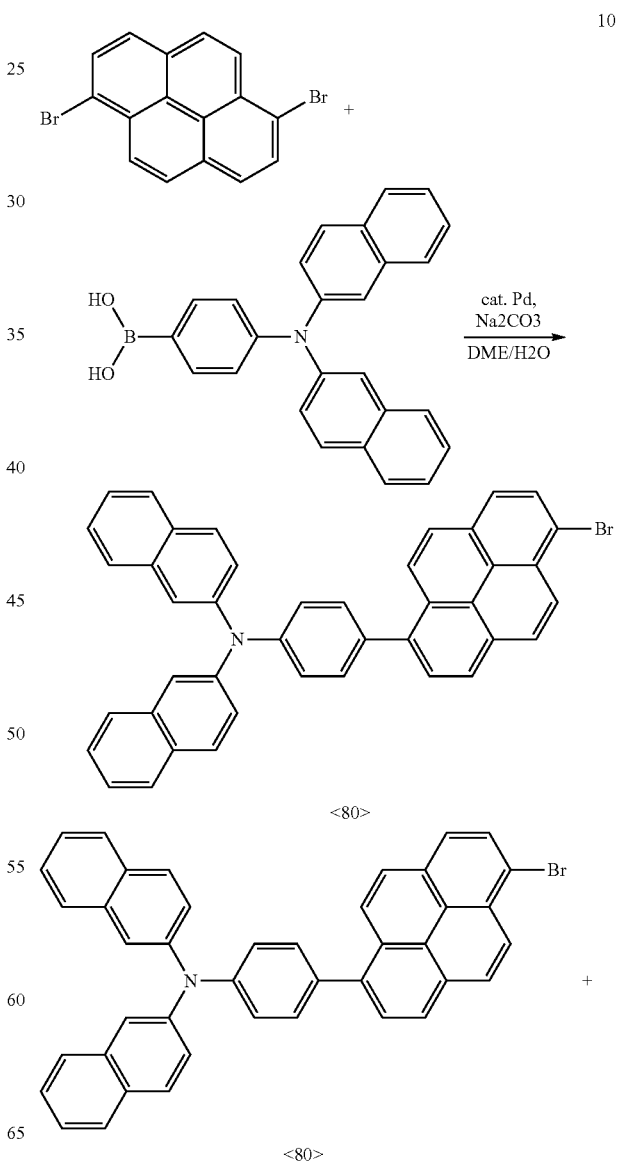

-continued

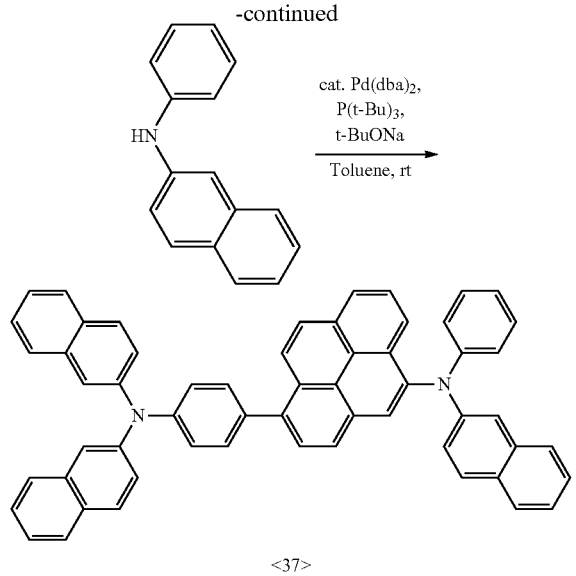

<37>

SYNTHESIS EXAMPLE 8

Synthesis of Compound of Formula 41

The overall synthesis process is shown in the reaction schemes 11 and 12. 4'-(di-naphthalene-2-yl-amino)-biphenyl-4-boronic acid, represented by the formula 81, was synthesized by a known esterification of boronic acid method, through the route represented by the reaction scheme 11.

As represented by the reaction schemes 12, the same procedure as in Synthesis Example 7 was conducted, except that 4'-(di-naphthalene-2-yl-amino)-biphenyl-4-boronic acid, represented by the formula 81, instead of 4-(di-naphthalene-2-yl-amino)-phenylboronic acid in the Suzuki-coupling reaction in Synthesis Example 7, was used. The target compound, {6-[4'-(di-naphthalene-2-yl-amino)-biphenyl-4-yl]-pyrene-1-yl}naphthalene-2-yl-phenyl-amine, represented by the formula 41, was obtained, as confirmed by MS (EI) calcd for $C_{64}H_{42}N_2$, 839.03; Found: 838.

11

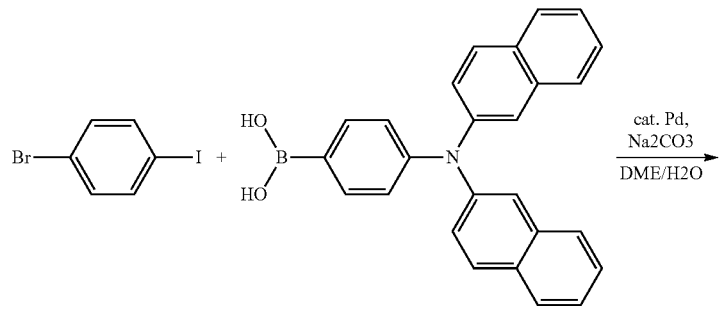

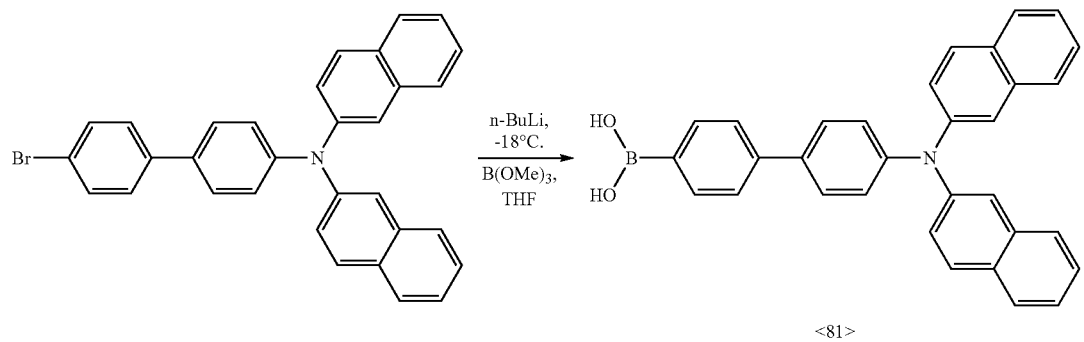

<81>

12

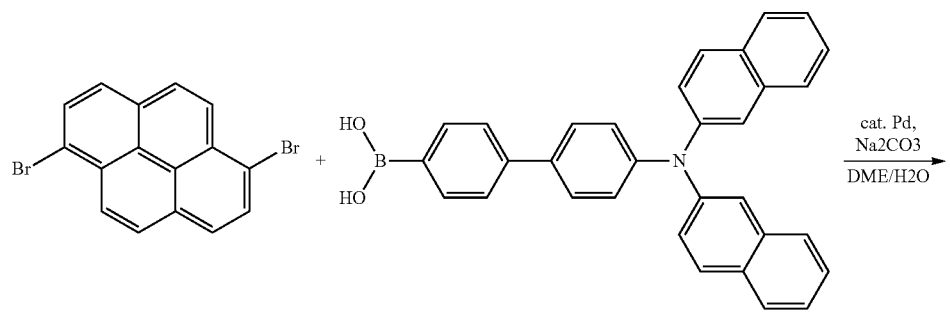

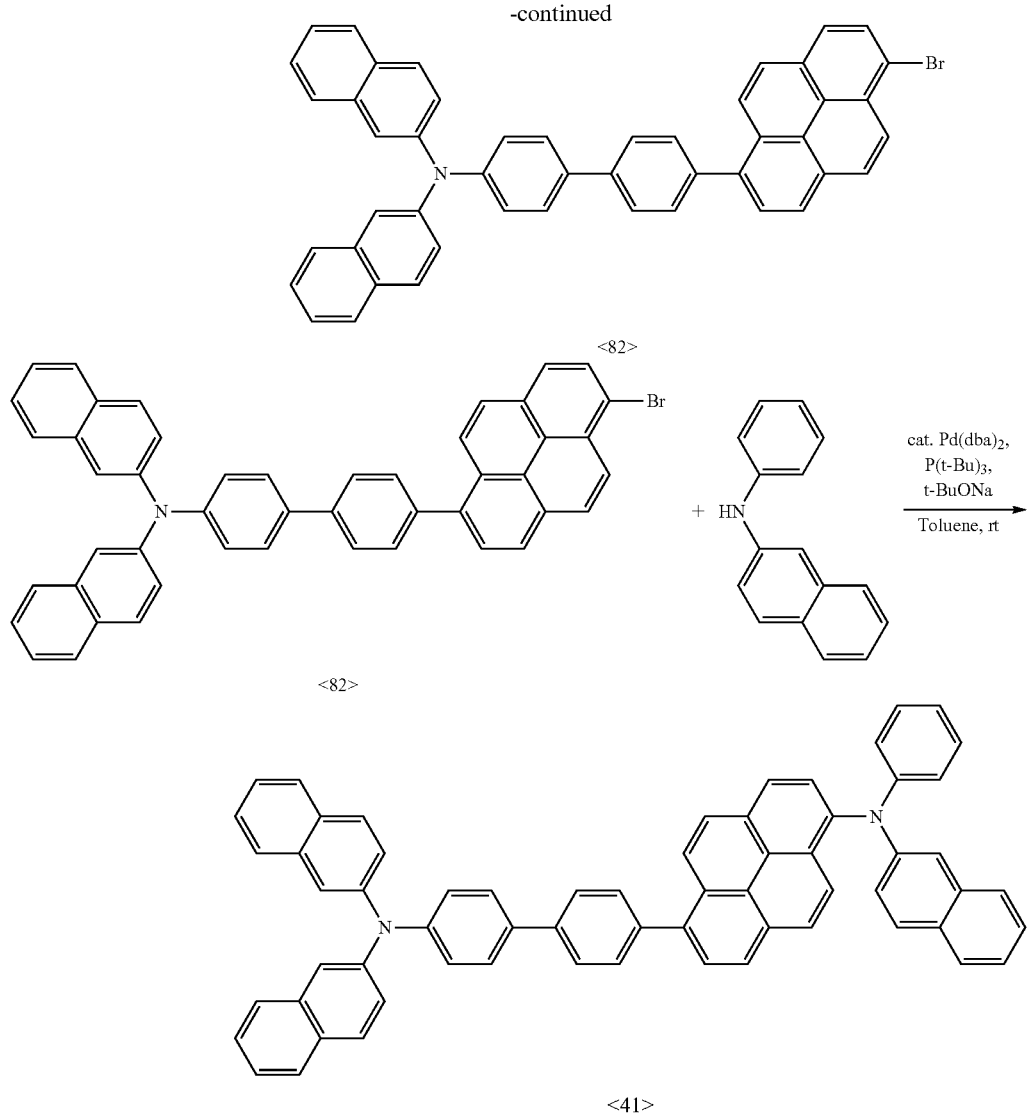

SYNTHESIS EXAMPLE 9

Synthesis of Compound of Formula 44

The overall synthesis process is shown in the reaction scheme 13.

First, 26.0 mmol of 1,6-dibromopyrene, 14.8 mmol of naphthalene-2-yl-phenyl-amine and catalytic amounts of bis(dibenzylidene acetone)-palladium, tri-t-butylphosphine and sodium-t-butoxide were placed into a 500 mL-3-neck flask under a nitrogen atmosphere, 200 mL of toluene was added thereto, followed by refluxing at 105° C. for 5 hours. After the reaction was completed, the reaction mixture was cooled to the room temperature, an excess of 1,6-dibromopyrene was collected by filtration, and a formed organic layer was extracted using distilled water and ethylacetate, dried with magnesium sulfate to then remove a solvent under reduced pressure. The resultant product was purified by column chromatography using ethylacetate and n-hexane, followed by vacuum drying, and the target compound, (6-bromo-pyrene-1-yl)-naphthalene-2-yl-phenylamine represented by the formula 83 was obtained (yield: 36%), as confirmed by MS (EI) calcd for $C_{32}H_{20}BrN$, 498.41; Found: 497.

Under the nitrogen atmosphere, 26.0 mmol of 1,6-dibromopyrene, 12.8 mmol of 4-diphenylamino-phenyl-1-boronic acid and a catalytic amount of tetrakis(triphenylphosphine)-palladium were placed into a 500 mL-3-neck flask, 225 mL of 1,2-dimethoxy ethane and 80 mL of 2M-sodium carbonate aqueous solution were added thereto, followed by refluxing at 95° C. for 20 hours. After the reaction was completed, the reaction mixture was cooled to the room temperature, an excess of 1,6-dibromopyrene was collected by filtration, and a formed organic layer was extracted using distilled water and ethylacetate, dried with magnesium sulfate to then remove a solvent under reduced pressure. The resultant product was purified by column chromatography using ethylacetate and n-hexane, followed by vacuum drying, and the target compound, [4-(6-bromo-pyrene-1-yl)-phenyl]-diphenylamine represented by the formula 84 was obtained (yield: 28%), as confirmed by MS (EI) calcd for $C_{34}H_{22}BrN$, 524.45; Found: 523.

A Grignard reaction is carried out on 3.8 mmol of (6-bromo-pyrene-1-yl)-naphthalene-2-yl-phenylamine represented by the formula 83 under a nitrogen atmosphere using 40 mL of an anhydrous tetrahydrofuran solvent. The formed product of the Grignard reaction was slowly added dropwise to an anhydrous tetrahydrofuran solution having 3.0 mmol of [4-(6-bromo-pyrene-1-yl)-phenyl]-diphenylamine represented by the formula 74 and a catalytic amount of [1,3-bis(diphenylphosphino)propane]nickel (II) dissolved therein using a cannula, followed by stirring for 4 hours. After the reaction was completed, a formed organic layer was extracted using distilled water and ethylacetate, dried with magnesium sulfate to then remove a solvent under reduced pressure. The resultant product was purified by column chromatography using ethylacetate and n-hexane, followed by vacuum drying, and the target compound, [6'-(4-diphenylamino-phenyl)-[1,1']bipyrene-yl-6-yl]-naphthalene-2-yl-phenylamine represented by the formula 44 was obtained, as confirmed by MS (EI) calcd for $C_{66}H_{42}N_2$, 863.05; Found: 862.

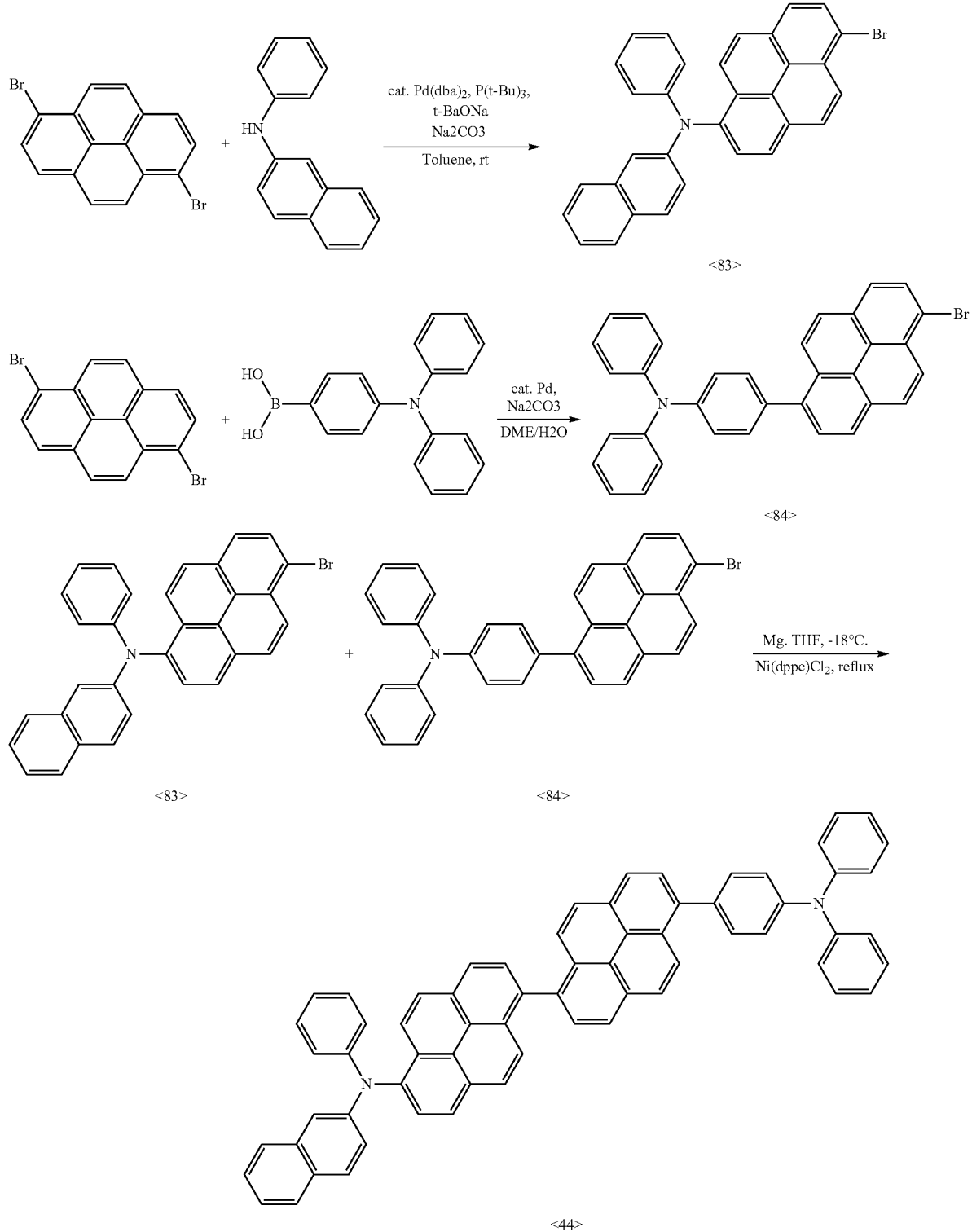

SYNTHESIS EXAMPLE 10

Synthesis of Compound of Formula 56

The overall synthesis process is shown in the reaction scheme 14. As represented by the reaction scheme 14, the same procedure as in Synthesis Example 4 was conducted, except that [4-(6-bromo-pyrene-1-yl)-phenyl]-di-naphthalene-2-yl-amine represented by the formula 80 was synthesized using 4-(di-naphthalene-2-yl-amino)-phenylboronic acid, instead of 4-(naphthalene-2-yl-phenyl-amino)-phenylboronic acid in the Suzuki-coupling reaction in Synthesis Example 4, and phenyl-quinoline-4-yl-amine, instead of naphthalene-1-yl-naphthalene-2-yl-amine in Synthesis Example 1, for an arylamination reaction. The target compound, {6-[4-(di-naphthalene-2-yl-amino)-phenyl]-pyrene-1-yl}-phenyl-quinoline-4-yl-amine, represented by the formula 56, was obtained, as confirmed by MS (EI) calcd for $C_{57}H_{37}N_3$, 763.92; Found: 763.

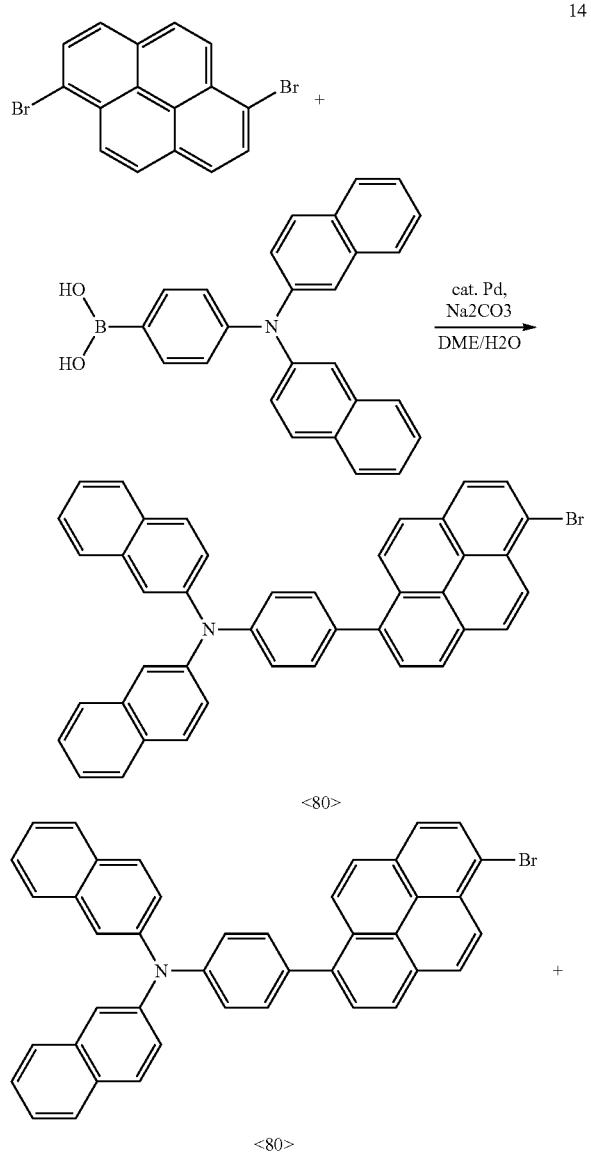

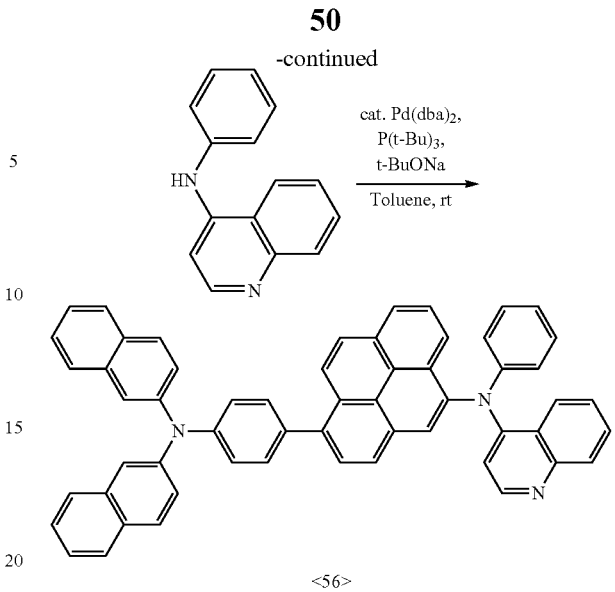

COMPARATIVE SYNTHESIS EXAMPLE 1

Synthesis of Compound of Formula 85

The overall synthesis process is shown in the reaction scheme 14.

2.00 g (5.6 mmol) of 1,6-dibromopyrene, 3.53 g (12.2 mmol) of 4-(diphenylamino)-phenylboronic acid and a catalytic amount of tetrakis(triphenylphosphine)palladium were placed into a 100 mL-3-neck flask under a nitrogen atmosphere, 40 mL of 1,2-dimethoxy ethane and 20 mL of 2M-sodium carbonate aqueous solution were added thereto, followed by refluxing at 95° C. for 20 hours. After the reaction was completed, the reaction mixture was cooled to the room temperature, and a formed organic layer was extracted using distilled water and ethylacetate, dried with magnesium sulfate to then remove a solvent under reduced pressure. The resultant product was reprecipitated using tetrahydrofuran and methanol for filtration, followed by vacuum drying, and 3.10 g of the target compound having the same substituted tertiary amine of the compound represented by the formula 85 was obtained (yield: 81%), as confirmed by MS (EI) calcd for $C_{52}H_{36}N_2$, 688.86; Found: 688.

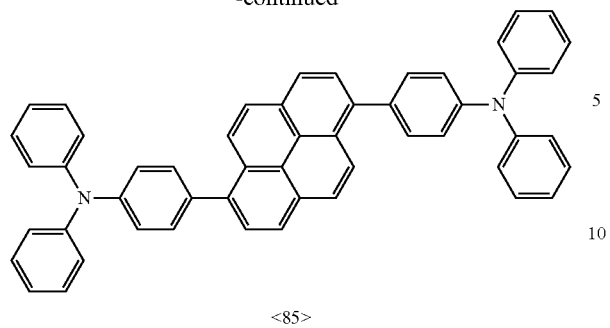

<85>

COMPARATIVE SYNTHESIS EXAMPLE 2

Synthesis of Compound of Formula 86

The overall synthesis process is shown in the reaction scheme 16.

2.00 g (5.6 mmol) of 1,6-dibromopyrene, 1.90 g (11.2 mmol) of diphenylamine, and catalytic amounts of bis(dibenzylidene acetone)-palladium, tri-t-butylphosphine, and sodium-t-butoxide were placed into a 100 mL-3-neck flask, a catalytic amount of tetrakis(triphenylphosphine)palladium were placed into a 100 mL-3-neck flask under a nitrogen atmosphere, 80 mL of toluene was added thereto, followed by stirring at room temperature for 8 hours. After the reaction was completed, the reaction mixture was cooled to the room temperature, and a formed organic layer was extracted using distilled water and ethylacetate, dried with magnesium sulfate to then remove a solvent under reduced pressure. The resultant product was reprecipitated using tetrahydrofuran and methanol for filtration, followed by vacuum drying, and 2.35 g of the target compound having the same substituted secondary amine of the compound, N,N,N',N'-tetraphenyl-pyrene-1,6-diamine represented by the formula 86, was obtained (yield: 74%), as confirmed by MS (EI) calcd for $C_{40}H_{28}N_2$, 536.66; Found: 535.

16

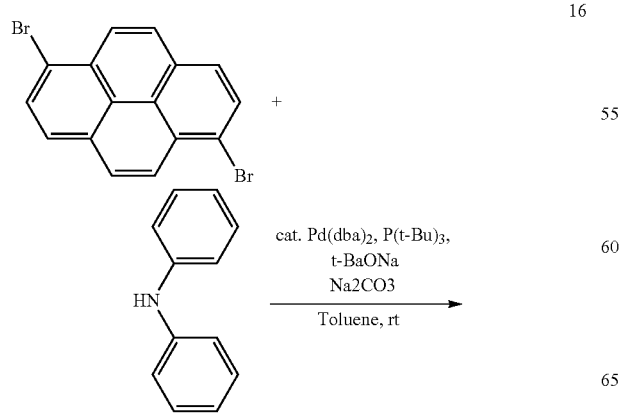

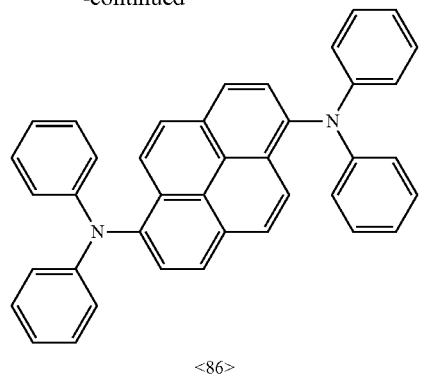

<86>

COMPARATIVE SYNTHESIS EXAMPLE 3

Synthesis of Compound of Formula 87

The overall synthesis process is shown in the reaction scheme 17. The same procedure as in Comparative Synthesis Example 2 was conducted, except that naphthalene-1-yl-phenylamine, instead of diphenylamine, was used in the arylamination reaction, and the target compound, N,N'-di-naphthalene-1-yl-N,N'-diphenyl-pyrene-1,6-diamine represented by the formula 87 having the same substituted secondary amine, was obtained, as confirmed by MS (EI) calcd for $C_{48}H_{32}N_2$, 636.78; Found: 636.

17

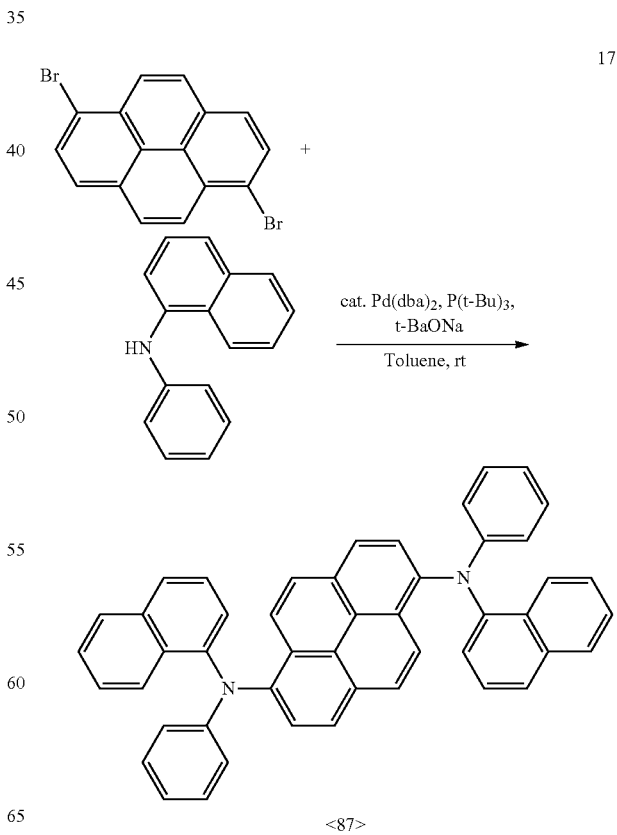

<87>

EXAMPLE 1

Fabrication and Evaluation of Organic EL Element 1

A glass substrate of 25 mm×25 mm size having an ITO transparent electrode coated with an insulation film was cleaned by application of ultrasonic wave in isopropyl alcohol for 5 minutes and then by exposure to ozone generated by ultraviolet light for 30 minutes. The cleaned glass substrate having an ITO transparent electrode line was fixed to a substrate holder of a vacuum deposition apparatus, and on the surface, where the ITO transparent electrode line was fixed, of the substrate, a film of 2-TNATA (4,4',4"-Tris(N-(2-naphthyl)-N-phenyl-amino)-tri-phenylamine) as a hole injecting material was formed to a thickness of 600 Å by a resistance heating deposition method so as to cover the transparent electrode. Subsequently, a film of NPD(N,N'-bis(naphthalen-1-yl)-N,N'-bis(phenyl)benzidine) as a hole transporting material was formed on the hole injecting material film to a thickness of 200 Å by the same deposition method as stated above. Concurrently, a layer was formed as light emitting layer to a thickness of 40 nm by a vapor deposition using a fluorescent host material represented by the formula 88 and the compound represented by the formula 22 synthesized in Synthesis Example 1 as a fluorescent dopant material (3 wt %). Subsequently, a film of Alq3 (tris-(8-hydroxyquinoline) aluminium-(III)) as an electron transporting material was formed to a thickness of 300 Å. Further, a Li film was formed to a thickness of 1 nm at a rate of 0.1 Å/sec and Al metal was deposited on the Li film to form a metal cathode having a thickness of 100 nm, thereby fabricating an organic EL device. The equipment used for deposition was an EL deposition device manufactured by VTS Corporation.

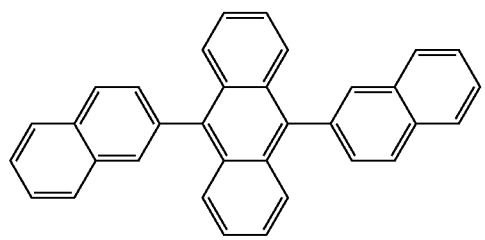

(88)

EXAMPLE 2

Fabrication and Evaluation of Organic EL Element 2

An organic EL element was fabricated in substantially the same method as in Example 1 except that the compound represented by the formula 23 synthesized in Synthesis Example 2 was used in place of the compound represented by the formula 22 synthesized in Synthesis Example 1.

EXAMPLE 3

Fabrication and Evaluation of Organic EL Element 3

An organic EL element was fabricated in substantially the same method as in Example 1 except that the compound represented by the formula 24 synthesized in Synthesis Example 3 was used in place of the compound represented by the formula 22 synthesized in Synthesis Example 1.

EXAMPLE 4

Fabrication and Evaluation of Organic EL Element 4

An organic EL element was fabricated in substantially the same method as in Example 1 except that the compound represented by the formula 29 synthesized in Synthesis Example 4 was used in place of the compound represented by the formula 22 synthesized in Synthesis Example 1.

EXAMPLE 5

Fabrication and Evaluation of Organic EL Element 5

An organic EL element was fabricated in substantially the same method as in Example 1 except that the compound represented by the formula 35 synthesized in Synthesis Example 5 was used in place of the compound represented by the formula 22 synthesized in Synthesis Example 1.

EXAMPLE 6

Fabrication and Evaluation of Organic EL Element 6

An organic EL element was fabricated in substantially the same method as in Example 1 except that the compound represented by the formula 36 synthesized in Synthesis Example 6 was used in place of the compound represented by the formula 22 synthesized in Synthesis Example 1.

EXAMPLE 7

Fabrication and Evaluation of Organic EL Element 7

An organic EL element was fabricated in substantially the same method as in Example 1 except that the compound represented by the formula 37 synthesized in Synthesis Example 7 was used in place of the compound represented by the formula 22 synthesized in Synthesis Example 1.

EXAMPLE 8

Fabrication and Evaluation of Organic EL Element 8

An organic EL element was fabricated in substantially the same method as in Example 1 except that the compound represented by the formula 41 synthesized in Synthesis Example 8 was used in place of the compound represented by the formula 22 synthesized in Synthesis Example 1.

EXAMPLE 9

Fabrication and Evaluation of Organic EL Element 9

An organic EL element was fabricated in substantially the same method as in Example 1 except that the compound represented by the formula 44 synthesized in Synthesis Example 9 was used in place of the compound represented by the formula 22 synthesized in Synthesis Example 1.

EXAMPLE 10

Fabrication and Evaluation of Organic EL Element 10

An organic EL element was fabricated in substantially the same method as in Example 1 except that the compound represented by the formula 56 synthesized in Synthesis Example 10 was used in place of the compound represented by the formula 22 synthesized in Synthesis Example 1.

COMPARATIVE EXAMPLE 1

Fabrication and Evaluation of Organic EL Element 11

An organic EL element was fabricated in substantially the same method as in Example 1 except that the compound represented by the formula 85 synthesized in Comparative Synthesis Example 1 was used in place of the compound represented by the formula 22 synthesized in Synthesis Example 1.

COMPARATIVE EXAMPLE 2

Fabrication and Evaluation of Organic EL Element 12

An organic EL element was fabricated in substantially the same method as in Example 1 except that the compound represented by the formula 86 synthesized in Comparative Synthesis Example 2 was used in place of the compound represented by the formula 22 synthesized in Synthesis Example 1.

COMPARATIVE EXAMPLE 3

Fabrication and Evaluation of Organic EL Element 13

An organic EL element was fabricated in substantially the same method as in Example 1 except that the compound represented by the formula 87 synthesized in Comparative Synthesis Example 3 was used in place of the compound represented by the formula 22 synthesized in Synthesis Example 1.

EXPERIMENTAL EXAMPLE

Characteristics of the organic EL elements fabricated in Examples 1 to 10 and Comparative Examples 1 to 3 were evaluated in the following manners, and the evaluation results are shown in Table 1.

1) Current Density

Changes in the current density depending on the voltage change were measured for the fabricated organic EL elements. The measurement was made by measuring values of voltage flowing through a cell using a current-voltage meter (Kethely 237) while varying the current density by 2.5 mA from 2.5 mA/cm² to 100 mA/cm².

2) Chromaticity Coordinates

Chromaticity coordinates of the fabricated organic EL elements were measured using a luminance colorimeter (PR650) while varying the current density by 2.5 mA from 2.5 mA/cm² to 100 mA/cm².

3) Luminance

Luminances of the fabricated organic EL elements were measured using a luminance colorimeter (PR650) by supplying power from a current-voltage meter (Kethely 237).

4) Efficiency of Light Emission

Efficiency of light emission was calculated using the measurement data of luminance and current density.

TABLE 1

| | Current density (mA/cm2) | Chromaticity coordinates CIE1931 (x, y) | Efficiency of light emission (cd/A) | Lifetime (@1000 nit) |
|---|---|---|---|---|
| Example 1 | 20 | (0.144, 0.123) | 3.82 | 500 |
| Example 2 | 20 | (0.142, 0.109) | 3.47 | 250 |
| Example 3 | 20 | (0.149, 0.118) | 3.62 | 350 |
| Example 4 | 20 | (0.144, 0.143) | 6.28 | 500 |
| Example 5 | 20 | (0.142, 0.135) | 6.57 | 800 |
| Example 6 | 20 | (0.153, 0.166) | 6.43 | 420 |
| Example 7 | 20 | (0.153, 0.158) | 6.70 | 600 |
| Example 8 | 20 | (0.148, 0.148) | 6.40 | 480 |
| Example 9 | 20 | (0.153, 0.168) | 8.30 | 500 |
| Example 10 | 20 | (0.153, 0.134) | 5.80 | 450 |
| Comparative Example 1 | 20 | (0.173, 0.164) | 4.29 | 60 |
| Comparative Example 2 | 20 | (0.150, 0.168) | 5.41 | 400 |
| Comparative Example 3 | 20 | (0.150, 0.154) | 2.32 | 10 |

As confirmed from the results shown in Table 1, the asymmetric aryamine derivatives having different substituent groups of a secondary amine and a tertiary amine induced to an aryl compound Ar core so that they do not include a symmetrical axis and a symmetrical surface in a molecule, can be applied to organic thin layers of organic EL elements. In addition, when an organic EL element is fabricated using the organic thin layer as a light-emitting layer, the organic EL element emits light in a blue wavelength region and exhibits excellent color purity, remarkably improved efficiency of light emission and long lifetime. In particular, the organic EL elements fabricated in Examples 1 to 10 in which the asymmetric arylamine derivatives according to the present invention were used, exhibited remarkably improved color purity, efficiency of light emission and long lifetime characteristics, compared to the conventional organic EL elements fabricated in Comparative Examples 1 to 3 in which arylamine derivative structures having the same secondary or tertiary amine induced to pyrene compounds.

While the invention has been described in detail and with reference to specific embodiments thereof, it will be apparent to one skilled in the art that various changes and modifications can be made therein without departing from the spirit and scope of the invention.

The invention claimed is:

1. An asymmetric arylamine derivative for an organic electroluminescent element, represented by the formula (1) with the proviso that the arylamine derivative does not include a symmetrical axis and a symmetrical surface in a molecule by inducing a secondary amine and a tertiary amine to an aryl compound (Ar) core:

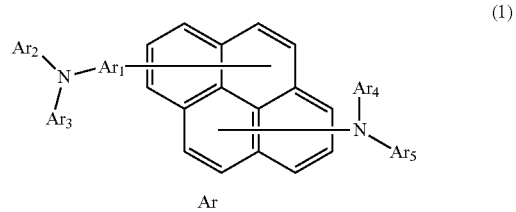

(1)

wherein Ar is pyrene,
Ar₁ is an aryl group selected from the group consisting of an aryl group represented by the formula (4), an aryl group represented by the formula (5), an aryl group represented by the formula (6), an aryl group represented by the formula (7), an aryl group represented by the formula (8), an aryl group represented by the formula (9), an aryl group represented by the formula (10), an aryl group represented by the formula (11), and an aryl group in which at least two of the aryl groups represented by the formulas (4) to (11) are combined, and $Ar_2$ to $Ar_5$ each independently represents a divalent $C_6$-$C_{30}$ aryl group, at least one of $Ar_2$ to $Ar_5$ having a different structure when the secondary amine and the tertiary amine in Ar are substituted at symmetrical positions, and $Ar_2$ to $Ar_5$ having the same structure or different structures when the secondary amine and the tertiary amine in Ar are substituted at asymmetrical positions:

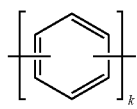
(4)

wherein k represents an integer of 1 to 3;

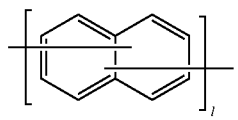
(5)

wherein I represents an integer of 1 or 2;

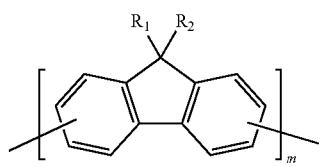
(6)

wherein m represents an integer of 1 or 2, $R_1$ and $R_2$ are each independently selected from the group consisting of a $C_1$-$C_{20}$ alkyl group, a $C_6$-$C_{20}$ cycloalkyl group capable of forming a unsaturated ring, a $C_1$-$C_{20}$ alkoxy group, and a $C_6$-$C_{12}$ aryl group;

(7)

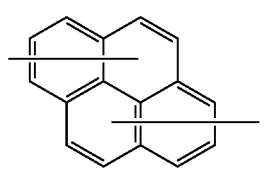
(8)

wherein n represents an integer of 1 to 3;

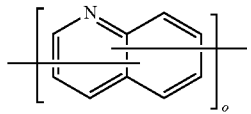
(9)

wherein o represents an integer of 1 or 2;

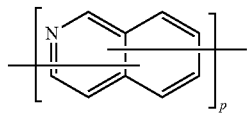
(10)

wherein p represents an integer of 1 or 2; and

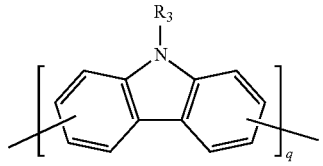
(11)

wherein q represents an integer of 1 or 2, and $R_3$ is a $C_1$-$C_{20}$ alkyl group or a $C_6$-$C_{12}$ aryl group.

2. The asymmetric arylamine derivative of claim 1, wherein $Ar_2$ to $Ar_5$ each independently represents a divalent $C_6$-$C_{30}$ aryl group selected from the group consisting of an aryl group represented by the formula (12), an aryl group represented by the formula (13), an aryl group represented by the formula (14), an aryl group represented by the formula (15), an aryl group represented by the formula (16), an aryl group represented by the formula (17), an aryl group represented by the formula (18), an aryl group represented by the formula (19), and an aryl group in which at least two of the aryl groups represented by the formulas (12) to (19) are combined, at least one of $Ar_2$ to $Ar_5$ having a different structure when the secondary amine and the tertiary amine in Ar of the formula (1) are substituted at symmetrical positions, and $Ar_2$ to $Ar_5$ having the same structure or different structures when the secondary amine and the tertiary amine in Ar are substituted at asymmetrical positions:

(12)

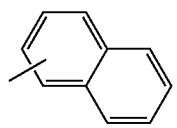
(13)

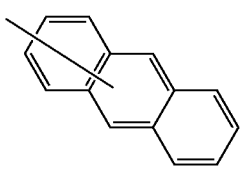
(14)

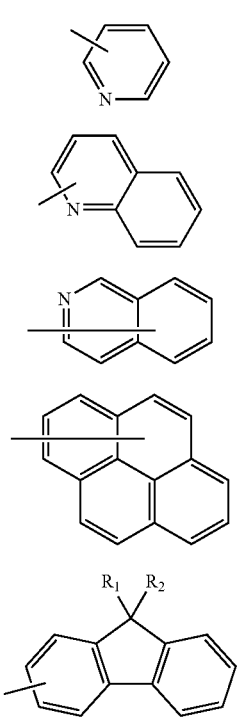

(15)

(16)

(17)

(18)

(19)

wherein $R_1$ and $R_2$ are each independently selected from the group consisting of a $C_1$-$C_{20}$ alkyl group, a $C_6$-$C_{20}$ cycloalkyl group capable of forming a unsaturated ring, a $C_1$-$C_{20}$ alkoxy group, and a $C_6$-$C_{12}$ aryl group.

3. The asymmetric arylamine derivative of claim 1, wherein in the formula (1), Ar, $Ar_1$, $Ar_2$, $Ar_3$, $Ar_4$, and $Ar_5$ have each independently at least one hydrogen substituted by a substituent selected from the group consisting of deuterium atom, a halogen atom, a nitro group, a $C_1$-$C_{20}$ alkyl group, a $C_6$-$C_{20}$ cycloalkyl group, a $C_1$-$C_{20}$ alkoxy group, a cyano group, a trifluoromethyl group, an alkylsilyl group having a $C_1$-$C_6$ alkyl group, and an arylsilyl group having $C_4$-$C_8$ hetero atoms.

4. A manufacturing method of an arylamine derivative for an organic electroluminescent element, represented by the formula (1) with the proviso that the arylamine derivative does not include a symmetrical axis and a symmetrical surface in a molecule:

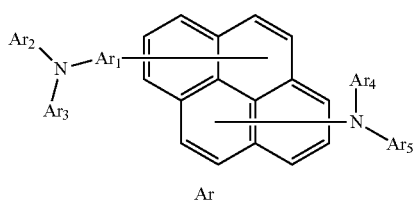

(1)

wherein Ar is pyrene,
$Ar_1$ is an aryl group selected from the group consisting of an aryl group represented by the formula (4), an aryl group represented by the formula (5), an aryl group represented by the formula (6), an aryl group represented by the formula (7), an aryl group represented by the formula (8), an aryl group represented by the formula (9), an aryl group represented by the formula (10), an aryl group represented by the formula (11), and an aryl group in which at least two of the aryl groups represented by the formulas (4) to (11) are combined, and
$Ar_2$ to $Ar_5$ each independently represents a divalent $C_6$-$C_{30}$ aryl group, at least one of $Ar_2$ to $Ar_5$ having a different structure when the secondary amine and the tertiary amine in Ar are substituted at symmetrical positions, and $Ar_2$ to $Ar_5$ having the same structure or different structures when the secondary amine and the tertiary amine in Ar are substituted at asymmetrical positions, the asymmetric arylamine derivative prepared by sequentially subjecting a starting material, an aryl compound (Ar) core di-substituted with the same functional group or different functional groups, to an aryl amination reaction or a Suzuki-coupling reaction, as represented by reaction scheme 1:

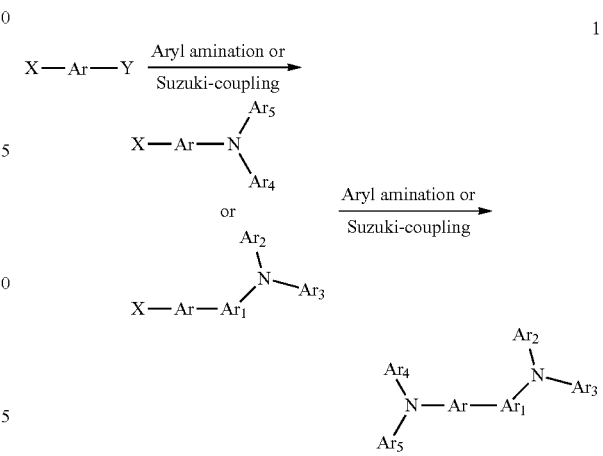

1 wherein X and Y represent the same group or different groups enabling an aryl amination reaction,
Ar is a divalent aryl group selected from the group consisting of naphthalene and pyrene,
$Ar_1$ is an aryl group selected from the group consisting of an aryl group represented by the formula (4), an aryl group represented by the formula (5), an aryl group represented by the formula (6), an aryl group represented by the formula (7), an aryl group represented by the formula (8), an aryl group represented by the formula (9), an aryl group represented by the formula (10), an aryl group represented by the formula (11), and an aryl group in which at least two of the aryl groups represented by the formulas (4) to (11) are combined, and
$Ar_2$ to $Ar_5$ each independently represents a divalent $C_6$-$C_{30}$ aryl group, at least one of $Ar_2$ to $Ar_5$ having a different structure when the secondary amine and the tertiary amine in Ar are substituted at symmetrical positions, and $Ar_2$ to $Ar_5$ having the same structure or different structures when the secondary amine and the tertiary amine in Ar are substituted at asymmetrical positions:

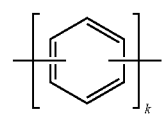

(4)

wherein k represents an integer of 1 to 3;

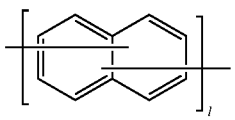 (5)

wherein I represents an integer of 1 or 2;

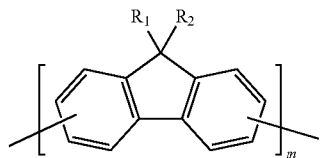 (6)

wherein m represents an integer of 1 or 2, $R_1$ and $R_2$ are each independently selected from the group consisting of a $C_1$-$C_{20}$ alkyl group, a $C_6$-$C_{20}$ cycloalkyl group capable of forming a unsaturated ring, a $C_1$-$C_{20}$ alkoxy group, and a $C_6$-$C_{12}$ aryl group;

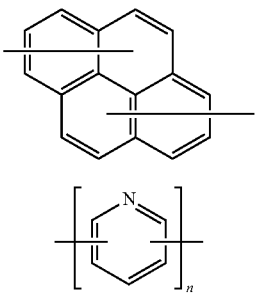 (7)

(8)

wherein n represents an integer of 1 to 3;

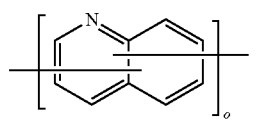 (9)

wherein o represents an integer of 1 or 2;

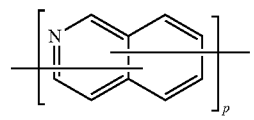 (10)

wherein p represents an integer of 1 or 2; and

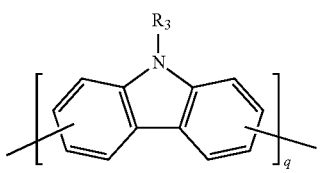 (11)

wherein q represents an integer of 1 or 2, and $R_3$ is a $C_1$-$C_{20}$ alkyl group or a $C_6$-$C_{12}$ aryl group.

5. The manufacturing method of claim 4, wherein X and Y represent the same group or different groups selected from a halogen, amine and hydroxyl group, enabling an aryl amination reaction.

6. An organic thin layer material for an organic electroluminescent element, organic thin layer material comprising the asymmetric arylamine derivative of claim 1.

7. The organic thin layer material of claim 6, the organic thin layer material being a light-emitting material or a dopant material.

8. An organic electroluminescent device comprising an anode, a cathode and multiple organic thin layers between the anode and the cathode, wherein at least one of the multiple organic thin layers includes the asymmetric arylamine derivative of claim 1.

9. The organic electroluminescent device of claim 8, wherein the multiple organic thin layers include at least one selected from a hole injection layer, a hole transport layer, a light-emitting layer, an electron injection layer and an electron transport layer.

10. The organic electroluminescent device of claim 8, wherein the organic thin layers are light-emitting layers.

11. The organic electroluminescent device of claim 8, wherein the organic thin layers include a host compound and a dopant compound.

* * * * *